US008129675B2

(12) United States Patent
Schultz et al.

(10) Patent No.: US 8,129,675 B2
(45) Date of Patent: Mar. 6, 2012

(54) NEUTRAL/ION REACTOR IN ADIABATIC SUPERSONIC GAS FLOW FOR ION MOBILITY TIME-OF-FLIGHT MASS SPECTROMETRY

(75) Inventors: J. Albert Schultz, Houston, TX (US); Valeriy V. Raznikov, Moscow (RU); Thomas F. Egan, Houston, TX (US); Michael V. Ugarov, Houston, TX (US); Agnès Tempez, Massy (FR); Marina O. Raznikova, Moscow (RU); Vladislav V. Zelenov, Moscow (RU); Alexander R. Pikhtelev, Chernogolovka (RU); Valerie E. Vaughn, Pearland, TX (US)

(73) Assignee: Ionwerks, Inc., Houston, TX (US)

( * ) Notice: Subject to any disclaimer, the term of this patent is extended or adjusted under 35 U.S.C. 154(b) by 251 days.

(21) Appl. No.: 12/483,831

(22) Filed: Jun. 12, 2009

(65) Prior Publication Data

US 2009/0309015 A1 Dec. 17, 2009

Related U.S. Application Data

(63) Continuation of application No. 11/771,711, filed on Jun. 29, 2007, now Pat. No. 7,547,878.

(60) Provisional application No. 60/817,338, filed on Jun. 29, 2006.

(51) Int. Cl.
*H01J 49/42* (2006.01)
*H01J 49/26* (2006.01)
*H01J 49/10* (2006.01)

(52) U.S. Cl. ........ 250/282; 250/281; 250/288; 250/287; 250/423 R; 250/424

(58) Field of Classification Search .................. 250/281, 250/288, 287, 423 R, 424
See application file for complete search history.

(56) References Cited

U.S. PATENT DOCUMENTS

| | | | |
|---|---|---|---|
| 5,477,046 A | 12/1995 | Dietrich et al. | |
| 6,674,069 B1 | 1/2004 | Martin et al. | |
| 6,797,948 B1 | 9/2004 | Wang | |
| 6,906,324 B1 | 6/2005 | Wang et al. | |
| 6,919,562 B1 * | 7/2005 | Whitehouse et al. | 250/288 |
| 6,959,248 B2 | 10/2005 | Gard et al. | |
| 7,034,292 B1 * | 4/2006 | Whitehouse et al. | 250/289 |
| 7,547,878 B2 * | 6/2009 | Schultz et al. | 250/282 |
| 2001/0032929 A1 | 10/2001 | Fuhrer et al. | |
| 2004/0245460 A1 | 12/2004 | Tehlirian et al. | |
| 2005/0127289 A1 | 6/2005 | Fuhrer et al. | |
| 2005/0230614 A1 | 10/2005 | Glukhoy | |
| 2005/0236578 A1 | 10/2005 | Kawato | |
| 2009/0072133 A1 * | 3/2009 | Schultz et al. | 250/282 |

OTHER PUBLICATIONS

International Search Report issued during the prosecution of International Application No. PCT/US07/72520.
Written Opinion issued during the prosecution of International Application No. PCT/US07/72520.
International Preliminary Report on Patentability issued Jan. 6, 2009, during the prosecution of International Application No. PCT/US2007/072520. Published Jan. 6, 2009.

* cited by examiner

*Primary Examiner* — Nikita Wells
(74) *Attorney, Agent, or Firm* — Fulbright & Jaworski L.L.P.

(57) ABSTRACT

The content of the invention comprises a concept of reactor for isolated ion transformations induced by collisions with neutral species. This reactor is also an interface between mobility cell and orthogonal injection TOFMS based on supersonic adiabatic gas flow with variable controlled composition directed along the axis of a multipole ion guide with sectioned rods for possibility of creating of controlled distributions of RF, DC and AC rotating fields.

21 Claims, 16 Drawing Sheets

NEUTRAL/ION REACTOR IN ADIABATIC SUPERSONIC GAS FLOW FOR ION MOBILITY TIME-OF-FLIGHT MASS SPECTROMETRY

CROSS-REFERENCE TO RELATED APPLICATIONS

This application claims priority to, and is a continuation of, U.S. application Ser. No. 11/771,711, filed on Jun. 29, 2007, now U.S. Pat. No. 7,547,878, claims priority to U.S. application Ser. No. 60/817,338, filed on Jun. 29, 2006.

STATEMENT REGARDING FEDERALLY SPONSORED RESEARCH OR DEVELOPMENT

This invention was made in part with government support. The United States Government has may have certain rights in the invention.

TECHNICAL FIELD

The present invention relates generally to instrumentation and methodology for characterization of chemical samples based on ion mobility spectrometry (IMS) and mass spectrometry (MS).

BACKGROUND OF THE INVENTION

An ion mobility spectrometer typically comprises an ionization source, a drift cell, and an ion detector. Examples of an ion detector include a faraday sampling plate or cup, an electron multiplier, or a mass spectrometer. Ion mobility spectrometry characterizes ions which are forced by an electric field to move a drift/buffer gas by measuring the ion's equilibrium drift velocity. When gaseous ions in the presence of the drift gas experience a constant electric field, they accelerate until the occurrence of a collision with a neutral atom or molecule within the drift gas. This acceleration and collision sequence is repeated continuously. Over time, this microscopic scenario averages the instantaneous velocities over the macroscopic dimensions of the drift tube resulting in the measurement of a constant ion velocity based upon ion size, charge and drift gas pressure. The ratio of the ion velocity to the magnitude of the electric field is defined as ion mobility. In other words, the ion drift velocity ($v_d$) is proportional to the electric field strength (E), where the ion mobility $K=v_d/E$ is a function of ion volume/charge ratio. Thus IMS is a separation technique similar to mass spectrometry. IMS is generally known to have high sensitivity with moderate resolving power. Separation efficiency is compromised when "bands" of ions spread apart as opposed to arriving together at the end of the IM drift tube in a tight, well-defined spatial region.

The resolving power of an ion mobility cell increases as the square root of the voltage when a uniform (or quasi-uniform) electric field is imposed across an ion mobility cell. It would seem that there is not much freedom to increase the resolution; however, the situation may be improved if the ion drift in a gas flow is considered. Ions move against a counterflow of gas only if the field is stronger than a certain value specific for the mobility of the ions. Ions with lower mobility may be stationary or even move in the negative direction (with the gas flow). Therefore, better ion separation can be expected where the time of the mobility separation can be chosen suitable for specific applications and compatible with the time diagram of the ion detector operation. The problem is how to efficiently organize ion mobility separation using gas counter-flow.

Most often ion mobility separation is used with ion sources working under elevated pressure and the source pressure is often used when these ions are introduced into a mobility cell. There may be no gas counter-flow in such an application. On the other hand, drift gas counter-flow is inevitable when IMS is used for analysis of ions created in high vacuum ion sources such as a secondary ion source where secondary ions are created from a surface maintained in high vacuum and must then be moved against a counter-flow of gas into the ion mobility spectrometer. The main problem then is how to overcome the strong counter-flow and preserve ion throughput. It is quite natural to use a time varying electric field to gradually move ions from a pulsed ion formation region against the gas flow and into the IMS. Small ions need a relatively small field to overcome the gas flow without decomposing whereas larger ions can come to the entrance orifice later under the action of a stronger field. At the time of application of the larger field necessary to move the heavier ions, small ions are already inside the mobility cell and are not subjected to the strong field which would otherwise cause their fragmentation. Some separation of ions in addition to the usual mobility separation is achieved in this case, however, it is often rather small, because of the diffusion broadening during the initial ion cloud formation.

The combination of an ion mobility spectrometer (IMS) with a mass spectrometer (MS) is well known in the art. In 1961, Barnes et al. were among the first to combine these two separation methods. Such instruments allow for separation and analysis of ions according to both their mobility and mass, which is often referred to as two-dimensional separation or two-dimensional analysis. Young et al. realized that a time-of-flight mass spectrometer (TOFMS) and specifically an orthogonal TOFMS is the most preferred mass spectrometer type to be used in such combination because of its ability to detect simultaneously and very rapidly (e.g. with high scan rate) all masses emerging from the mobility spectrometer. The combination of a mobility spectrometer with a TOFMS is referred to as a Mobility-TOFMS. This prior art instrument comprised means for ion generation, a mobility drift cell, a TOFMS, and a small orifice for ion transmission from the mobility cell to the TOFMS.

In 2003, Loboda (U.S. Pat. No. 6,630,662) described a method for improving ion mobility separation by balancing ion drift motions provided by the influence of DC electric field and counter-flow of the gas. Using this balance, ions are at first accumulated inside an ion guide, preferably an RF-ion guide, and then, by changing the electric field or gas flow, the ions are gradually eluted from the ion guide to the mass spectrometer. Such type of ion accumulation is restricted to collecting relatively small number of ions due to space-charge effects. It also has some limitation in ion mass-to-charge (m/z) range because RF-focusing for a given RF-voltage has decreasing efficiency for larger mass ions which cannot be improved by increasing the RF-voltage due to the possibility of creating a glow discharge at the relatively high gas pressure inside the RF multipole. Unfortunately at lower pressure the influence of the gas flow on ions is less and the diffusion of the ions increase so trapping and separation of larger ions could be compromised. The time of ion accumulation and their storage in the RF-ion guide cannot be too long, otherwise ions would be partially lost due to diffusion into rods or walls confining the gas flow. For at least these reasons, this method has significant resolving power limitations. The instrumental improvements disclosed below eliminate these drawbacks.

Use of MS as a detector enables separation based on mass-to-charge (m/z) ratio after the separation based on ion mobility. Shoff and Harden pioneered the use of Mobility-MS in a mode similar to tandem mass spectrometry (MS/MS). In this mode, the mobility spectrometer is used to isolate a parent ion and the mass spectrometer is used for the analysis of fragment ions (also called daughter ions), which are produced by fragmentation of parent ions. Below this specific technique of operating a Mobility-MS is referred to as Mobility/MS, or as Mobility-TOF if the mass spectrometer is a TOFMS-type instrument. Other prior art instruments and methods using sequential IMS/MS analysis have been described (see, e.g., McKight, et al. Phys. Rev., 1967, 164, 62; Young, et al., J. Chem. Phys., 1970, 53, 4295; U.S. Pat. Nos. 5,905,258 and 6,323,482 of Clemmer et al.; PCT WO 00/08456 of Guevremont) but none combine the instrumental improvements disclosed here. When coupled with soft ionization techniques and the sensitivity improvements obtained through the use of the drift cell systems disclosed herein, the IMS/MS systems and corresponding analytical methods of the present invention offer significant analytical advantages over the prior art, particularly for the analysis of macromolecular species, such as biomolecules.

One challenge when building a Ion Mobility-MS system is to achieve high ion transmission from the mobility region into the MS region. It is at this interface that earlier uses of linear fields appear incongruous with the goal of maximizing ion throughput across the IMS/MS interface. The mobility section operates at typical pressures between 1 mTorr and 1000 Torr whereas the MS typically operates at pressures below $10^{-4}$ Torr. In order to maintain this difference in pressure it is necessary to restrict the cross-section of the exit orifice of the IM drift cell so that the region between the IM and the MS can be differentially pumped. Typically this orifice cross section is well below 1 mm$^2$. Hence it is desirable to focus the ions into a narrow beam before they reach the interface. Another essential property of the ion beam coming into an oTOFMS is the beam divergence, or the kinetic energy of ion motion in the plane orthogonal to the direction of their travel. This is the main factor responsible for the quality of mass spectra obtained in the orthogonal TOFMS. It is a subject of our two co-pending U.S. patent applications: U.S. application Ser. No. 11/441,766 filed May 26, 2006; and U.S. application Ser. No. 11/441,768 filed May 26, 2006 to achieve good ion beam properties by using ion cooling in supersonic adiabatic gas flow. Both of these applications are incorporated by reference as though fully set out herein.

Tandem mass spectrometry techniques typically involve the detection of ions that have undergone some structural change(s) in a mass spectrometer. Frequently, this change involves dissociating or fragmenting a selected precursor or parent ion and recording the mass spectrum of the resultant daughter fragment ions. The information in the fragment ion mass spectrum is often a useful aid in elucidating the structure of the precursor or parent ion. The general approach used to obtain a mass spectrometry/mass spectrometry (MS/MS or MS$^2$) spectrum is to isolate a selected precursor or parent ion with a suitable m/z analyzer, subject the precursor or parent ion to an energy source to effect the dissociation (e.g. energetic collisions with a neutral gas in order to induce dissociation), and finally to mass analyze the fragment or daughter ions in order to generate a mass spectrum. An additional stage of isolation, fragmentation and mass analysis can be applied to the MS/MS scheme outlined above, giving MS/MS/MS or MS$^3$. This additional stage can be quite useful to elucidate dissociation pathways, particularly if the MS$^2$ spectrum is very rich in fragment ion peaks or is dominated by primary fragment ions with little structural information. MS$^3$ offers the opportunity to break down the primary fragment ions and generate additional or secondary fragment ions that often yield the information of interest. The technique can be carried out n times to provide an MS$^n$ spectrum.

Ions are typically fragmented or dissociated in some form of a collision cell where the ions are caused to collide with an inert gas. Dissociation is induced usually either because the ions are injected into the cell with a high axial energy or by application of an external excitation. See, for example, WIPO publication WO 00/33350 dated Jun. 8, 2000 by Douglas et al. Douglas discloses a triple quadrupole mass spectrometer wherein the middle quadrupole is configured as a relatively high pressure collision cell in which ions are trapped. This offers the opportunity to both isolate and fragment a chosen ion using resonant excitation techniques. The problem with the Douglas system is that the ability to isolate and fragment a specific ion within the collision cell is relatively low. To compensate for this, Douglas uses the first quadrupole as a mass filter to provide high resolution in the selection of precursor ions, which enables an MS$^2$ spectrum to be recorded with relatively high accuracy. However, to produce an MS$^3$ (or higher) spectrum, isolation and fragmentation must be carried out in the limited-resolution collision cell.

A three-dimensional ion trap (3-D IT) is one of the most flexible devices for MS-MS and multi-step (MS$^n$) analysis. The basic operation principle of the quadrupole ion trap mass spectrometer is well-known (for example, refer to U.S. Pat. No. 2,939,952, Paul et al., June, 1960). This trap is composed of a ring electrode and two end cap electrodes of special shape to create a quadrupolar distribution of potential. Radio frequency (RF) and DC offset electric potentials are applied between electrodes and cause ions to oscillate within the trap. By appropriately selecting voltage parameters, ions of a specific mass/charge ratio can be made to have stable or unstable trajectories. In another implementation an additional (auxiliary) AC voltage is applied to the end-caps to induce resonant excitation of selected ions either for the purpose of ejecting the selected ions or for the purpose of inducing collisional dissociation. The 3-D ion trap is capable of single step mass spectrometric analysis. In such analysis ions are injected into the trap (or generated within the trap), confined to the center of trap because of low energy collisions with an inert gas such as helium (typically at 1 mtorr pressure) and then sequentially ejected through the apertures in the end cap electrodes onto an external detector by raising the amplitude of the RF field. The same device could be used for a multi-step, i.e. MS$^n$, analysis—U.S. reissued Pat. No. 34,000, Syka et al., July, 1992. The ion trap isolates ions in a m/z window by rejecting other components, then fragments these isolated ions by AC excitation, then isolates resulting ion fragments in a m/z window and repeats such sequence (MS$^n$ operation) in a single cell. At the end of the sequence ions are resonantly ejected to acquire the mass spectrum of N-th generation fragments. The 3-D IT is vulnerable to sensitivity losses due to ion rejection and instability losses at the time of ion selection and fragmentation.

Another version of this technique is provided by hybrid instruments combining quadrupoles with time of flight analyzers (Q-TOF) where the second quadrupole mass spectrometer (in a triple quadrupole systems) is replaced by an orthogonal time of flight spectrometer (o-TOF). The o-TOF back end allows observation of all fragment ions at once and the acquisition of secondary spectra at high resolution and mass accuracy. The Q-TOF has huge advantages in cases where the full mass range of daughter ions is required, for example, for peptide sequencing, the Q-TOF strongly surpasses the performance of the triple quadrupole. However, the Q-TOF suffers a 10 to a 100 fold loss in sensitivity as compared to a single quadrupole mass filter operating in selected reaction monitoring mode (monitoring single m/z). For the same reason the sensitivity of the Q-TOF is lower in the mode of "parent scan" where, again, the second MS is used to monitor a single m/z. Usually, only one step of MS/MS analysis is possible for such types of instruments. Recently, the quadrupole has been replaced by a linear ion trap (LIT)—U.S. Pat. No. 6,020,586, Dresch et al., February, 2000. The quadrupole with electrostatic "plugs" is capable of trapping ions for long periods of time. The quadrupole field structure allows one to apply an arsenal of separation and excitation methods, developed in 3-D ion trap technology, combined with easy introduction and ejection of the ion beam out of the LIT. The LIT eliminates ion losses at selection and also can operate at poor vacuum conditions which reduces requirements on the pumping system. However, a limited resolution of ion selection, R<200, has been demonstrated thus far. A method for improving the sensitivity in LIT is described in U.S. Pat. No. 6,507,019, Chernushevich et al., January, 2003. According to this method, a voltage on the outlet of the collision chamber is controlled in synchronization with the timing of applying an acceleration voltage in a time-of-flight mass spectrometer thereby improving the sensitivity for ions in a specified range of m/z.

Fourier transform ion cyclotron resonance mass spectrometry (FTMS) currently provides the most accurate measurement of ion mass to charge ratios with a demonstrated resolution in excess of 100,000. In FTMS, ions are either injected from outside the cell or created inside the cell and confined in the cell by a combination of static magnetic and electric fields (Penning trap). The static magnetic and electric field define the mass dependent frequency of cyclotron motion. This motion is excited by an oscillating electric potential. After a short period the applied field is turned off. Amplifying and recording weak voltages induced on the cell plates by the ion's motion detects the frequency of ion motion and, thus, the m/z of the ion. Ions are selectively isolated or dissociated by varying the magnitude and frequency of the applied transverse RF electric potential and the background neutral gas pressure. Repeated sequences of ion isolation and fragmentation (MS$^n$ operation) can be performed in a single cell. The possibility of kinetic measurements of ion dissociation using controlled black body heating of ions so called BIRD technique is another unique property of these type instruments. However, it may be considered as rather basic research tool than analytically useful approach. An FTMS is a "bulky" device occupying a large footprint and is also expensive due to the costs of the magnetic field. Moreover, an FTMS exhibits poor ion retention in MS$^n$ operation (relative to the 3-D ion trap).

Use of an AC field for selected ion rotation within a gas filled RFQ axis has been described (Raznikov, et. al., RCM, 15, 1912-1921, 2001). Such ion motion was used for ion heating and fragmentation of selected ions by collisions with buffer gas. It was demonstrated that resolving power (FWHM) was near 80 for mass selecting the parent ions (within the m/z range 500-1000) which could then be selectively decomposed under $N_2$ pressure close to 20 mTorr. Kinetic measurements are enhanced when using this technique (Soulimenkov, et. al., Europian Journal of Mass Spectrometry 8, 99-105, 2002). Rotating ions around the axis of a gas filled RFQ is one of the particular cases of two-dimensional motion in an axially symmetric quadratic potential well provided by a quadrupolar RF-field. This motion is influenced by harmonic voltages applied to adjacent RFQ rods with phase shift π/2. Upon comparison with other types of ion oscillations in which the ion distance from RFQ axis varies over a wide range, ion rotation has some advantages conferred by the properties of classic harmonic motion. For simple ion oscillations (for dipole or quadrupole excitations), the ion velocity is not constant and the ions come to rest at the maximum deviation from the axis, whereas for rotating ion motion the velocity is almost constant. There are two advantages to having a constant average kinetic energy for a given maximum rotational orbit deviation from the axis. First, as a consequence of the constant ion velocity the conditions for observation of fragment ions, especially including low m/z values, can be considerably better known and controlled than merely using a quadrupolar field alone. Otherwise, in order to achieve the same average ion internal energy in the case of quadrupolar oscillations, it is necessary to have either larger maximum deviations of ions from the RFQ axis or to have a stronger ion focusing to the axis which then demands larger amplitude or lower frequency of the RF-voltage. The second advantage is that ion rotation gives more control of ion heating and decomposition under the usual conditions employed in the RFQ where the gas density is nearly uniform.

In addition to ICR mass spectrometry, other applications of ion rotation are found in DC traps like the Orbitrap instrument (disclosed by Makarov in 1999, U.S. Pat. No. 5,886,346) and FTMS based on ion rotation in a linear RF multipole ion trap (described by Park in 2004, U.S. Pat. No. 6,784,421). In all these instruments ions rotate freely in high vacuum after a short voltage pulse starts the ion motion. The linear RF multipole ion trap is the closest prior art to ion rotation in a gas filled RFQ. In both types of instrument the resolving power restrictions are dependent on the accuracy of manufacturing of RF ion guide or linear trap. The Orbitrap arguably has some important advantages over these techniques, however, it is limited to analyzing ions of only one sign while both ICR and ion rotation in linear multipole ion traps allow simultaneous measurement of ions of both signs. All these techniques may provide extremely high resolution for moderate to small ions. For larger ions mass resolving power decreases rapidly for two main reasons: large ions rotate at a lower frequency than smaller ions and larger m/z are more prone to oscillations and thus have shorter time periods of uninterrupted coherent motion due to the increased probability of impact with residual gas resulting from their larger collision cross section. Moreover, inserting large ions into the DC trap portion of the Orbitrap has a further limitation since these ions may have a large probability to collide with gas in the storage quadrupole during their acceleration to the necessary relatively high energy for insertion (about 1 kV). Thus, during insertion of these larger ions into the Orbitrap, a significant portion of the large ion flux may be lost due to dissociation broadening of their energy distribution away from an optimal insertion energy at the moment of their capture in the DC trap. These instruments demand long measurement times (up to few seconds) and slightly more time for ion preliminary accumulation. Thus, they are not suitable for many types of ion mobility measurements since all mobility resolution will be lost during such ion accumulation as will any information about the average velocity of the incoming ions. Also, most often mass spectrometric techniques provide only semi-quantitative information about ion transformations. For real kinetic measurements it is necessary to have very narrowly defined energy distributions (or temperatures) of ions and of neutral reactant components combined with precise measurement of reaction times. The only methods capable of manipulating these parameters use a direct heating of the reaction zone (like BIRD, for example). However, external heating of some parts of the instrument may result in significant experimental problems. The method of selective ion heating with a resonant rotating field also has a limited capability to specify both the temperature of the ions of interest and the time at which heating occurs since the temperature of rotating ions for a given field strength is dependent on ion mobility. Unfortunately, it is necessary to know this temperature under conditions when ions begin to decompose yet this temperature can only be effectively measured when ions have not yet decomposed. Furthermore, to have high selectivity with resonant ion rotation the buffer gas pressure should be small which then requires an inordinately long time for the selected ions to reach the desired steady state temperature. The same limitation occurs at the end of an RFQ when the rotating field is switched off to allow focusing the ions for subsequent measurement in the TOFMS.

Two dimensional, 2-D PAGE polyacrylamide gel electrophoresis is a popular and currently preferable technique for protein separation (Anderson N. G., Anderson N. L., Electrophoresis 1996; 17, 443453). Proteins are subjected at first to isoelectric focusing (IEF) in an immobilized pH gradient in the gel plate to separate proteins according to their charging abilities (pI values), a step which typically takes about 6-8 hours. Then, the IEF gel is placed on top of a gradient gel and is subjected to electrophoretic separation in the presence of SDS (sodium dodecyl sulphate). In SDS-PAGE, proteins are denatured and dissolved in a SDS buffer, negatively charged SDS molecules bind to the protein, with more molecules binding to larger proteins. On application of an electric field, proteins migrate in a polyactylamide gel according to their charge connected with size or mass. The electric field is switched off to immobilize the proteins within the gel. The separated proteins are stained for visualization, bands of interest are excised and digested with protease followed by mass spectrometry measurements for protein identification (Shevchenko, A., Jensen, O. N., Podtelejnikov, A. V., Sagliocco, F., Wilm, M., Vorm, O., Mortensen, P., Boucherie, H., Mann, M., Proc. Natl. Acad. Sci. U.S.A. 1996, 93, 14440-14445; Jensen, O. N., Larsen, M. R., Roepstorff, P., PROTEINS 1998, 74-89 Suppl. 2). 2-D PAGE is the current technology of choice for large scale proteomics analysis because 2-D PAGE at the moment is the highest resolution method for protein separation and the spots of proteins in the 2-D map are related to the properties of proteins, namely isoelectric point in the first dimension and the molecular mass in the second dimension. Therefore, the positions of proteins in 2-D map correspond to their chemical and physical properties. These properties can be used to identify and characterize the proteins. 2-D PAGE has been used to analyze human plasma proteins, and the pI and molecular weight of proteins can be used for detection and diagnosis of diseases in clinical analysis (Rasmussen, R K., Ji, H., Eddes, J. S., Moritz, R L., Reid, G. E., Simpson, R. J., Dorow, D. S., Electrophoresis 1997, 18, 588-598). However, 2-D PAGE is a time consuming procedure which is difficult to automate, it also suffers from limitations in sensitivity and dynamic range of detection. Virtual 2-D gel electrophoresis has recently been developed (Ogorzalek-Loo, R. R., Cavalcoli, J. D., VanBogelen, R A., Mitchell, C., Loo, J. A., Moldover, B., Andrews, P. C., Anal. Chem. 2001, 73, 40634070), where mass spectrometry replaces the size-based separation of SDS-PAGE in the second dimension. It has been shown that this technology is more sensitive than 2-D PAGE. However, the first dimension of separation is still performed in a polyacrylamide gel, limiting the potential for high throughput analysis. Capillary isoelectric focusing (CIEF) is an equilibrium-based method of separation that depends on a pH gradient created by carrier ampholyte. Proteins move under an electric field to their pI points where they carry zero average charge and are focused. Therefore, separation and concentration occur at the same time. The concentration of proteins at the focused zone can be increased by 100-500 times relative to the starting solution because the same protein in the whole capillary is focused on a single spot. Single point detection techniques, such as laser induced fluorescence and ESI-MS, have been employed to detect the separated proteins after CIEF. Focused protein zones need to be mobilized in order to pass through the detection point at the end of the tube (Rodriguez, R., Zhu, M., Wehr, T., J Chromatogr. A 1997, 772, 145-160). The problem of interfacing CIEF with MALDI-MS is also because the focused protein zone inside the capillary cannot be reached directly. Therefore, the contents of the capillary need to be moved out of the capillary and deposited into an appropriate surface for subsequent MALDI-MS analysis. This mobilization step degrades the resolution, increases the analysis time, and distorts the pH gradient. Hence, the result reproducibility is poor.

All of the above-referenced U.S. patents and published U.S. patent applications are incorporated by reference as though fully described herein.

Although much of the prior art has resulted in improvements in ion focusing, separation and in ion throughput from ion source to the mobility cell (and to the mass spectrometer in tandem instruments), there is room for additional improvement in all these areas. The inventors describe herein a concept and design of a new type of interface of an ion mobility cell with an orthogonal injection time-of-flight mass spectrometer (TOFMS) based on significant cooling of the ion beam in an adiabatic supersonic gas flow and its focusing by radio-frequency quadrupole or multipole ion guide with additional DC and AC rotating fields which result in variety of instrumental embodiments to provide improved ion production from investigated samples, their separation and measurements. The modified ion rotational trapping, manipulation, and measurement technique disclosed in the present invention is free from the limitations of the prior art as the mobility cross-sections of any ion of interest will have always been measured prior to its introduction into the RFM. Furthermore, the drift velocities of these ions and those for the components of the buffer gas and their divergences (which can be related to their temperatures) are essential for obtaining quantitative kinetic information and these properties can be uniquely measured by innovative use of multianode position sensitive detector combined with a multi-channel data recording system in a TOFMS. One of the aims of the present invention is to perform isoelectric separation of biomolecules in the gas phase and reduce the time of conventional procedure in gel separation from 6-8 hours to few seconds or minutes depending on the problem to be solved. Also the problems of interfacing of TOFMS with separating devices in liquid phase would be avoided in this case.

Time-of-flight instruments seem to be more suitable than prior art instruments for measurement of ions coming from an RF ion guide with supersonic gas flow, especially when investigation of large bioions is the main analytical problem. Divergence of large ions in the supersonic gas flow and their final focusing in an RF ion guide technically can be done significantly better than those for relatively small ions. Therefore, it is quite realistic to provide better resolving power for large ions in TOF measurements than for those ions with less mass and smaller size. Furthermore, the resolution of multi-charged ions varies proportionally to the square root of the charge number at least for a linear oTOFMS. Moreover, the expected peak shape, at least for a linear gridless TOFMS, would be close to Gaussian which is significantly better then Lorentzian peak shapes typical for FTMS instruments. This is an especially useful advantage when measuring a small peak adjacent to a large one. Multianode data acquisition allows not only to increase the dynamic range of the ion detection but also to measure ion velocities and their divergences thus providing direct estimations of their temperatures. These possibilities are important for quantitative kinetic measurements.

BRIEF SUMMARY OF THE INVENTION

The present invention is directed to a system and method for characterization of chemical samples based on ion mobility spectrometry (IMS) and mass spectrometry (MS).

In one embodiment of the present invention, there is an apparatus for the analysis of gaseous ions and neutral species and mixtures thereof, the apparatus comprising: an ion source for the production of gaseous ions and neutral species and mixtures thereof; a gas flow formation region fluidly coupled to the ion source, the gas flow formation region comprising a sectioned capillary having at least two electrodes, the gas flow formation region operable to accept ions and/or neutral species from the ion source; at least one sectioned radio-frequency multipole ion guide fluidly coupled to the gas flow formation region, the sectioned ion guide comprising a plurality of electrically isolated electrode sections; an exit orifice fluidly coupled to the at least one sectioned radio-frequency multipole ion guide; and, a detector fluidly coupled to the exit orifice. In some embodiments, the gas flow formation region comprises an input orifice. In some embodiments, the input orifice is coupled to a gas or liquid delivery valve. In some embodiments, the sectioned radio-frequency multipole ion guide comprises mulitelectrode rods. In some embodiments wherein the sectioned radio-frequency multipole ion guide comprises multielectrode rods, the mulitelectrode rods are separated by grounded plates isolated from ground. In some embodiments, the at least one sectioned radio-frequency multipole ion guide comprises a radio-frequency quadrupole. In some embodiments, the at least one sectioned radio-frequency multipole ion guide comprises a radio-frequency octapole. In some embodiments, the at least one sectioned radio-frequency multipole ion guide comprises a differential pumping region. In some embodiments, the electrically isolated electrode sections are coupled to a component selected from the group consisting of a DC voltage source, an AC voltage source, a RF voltage source, and any combination thereof. In some embodiments wherein the electrically isolated electrode sections are coupled to a component selected from the group consisting of a DC voltage source, an AC voltage source, a RF voltage source, and any combination thereof, the voltage sources are coupled to, and controlled by, a computer. In some embodiments, the gas flow formation region is a supersonic gas flow formation region. In some embodiments, the detector is a mass spectrometer. In some embodiments wherein the detector is a mass spectrometer, the mass spectrometer is an orthogonal time-of-flight mass spectrometer. In some embodiments wherein the detector is a mass spectrometer and the mass spectrometer is an orthogonal time-of-flight mass spectrometer, the orthogonal time-of-flight mass spectrometer comprises a position sensitive multianode detector. In some embodiments wherein the detector is a mass spectrometer and the mass spectrometer is an orthogonal time-of-flight mass spectrometer, the orthogonal time-of-flight mass spectrometer is a bipolar time-of-flight mass spectrometer. In some embodiments, the gas flow formation region comprises an exit capillary of the ion source. In some embodiments wherein the gas flow formation region comprises an exit capillary of the ion source, the exit capillary comprises individually biasable gas-tight electrodes. In some embodiments wherein the exit capillary comprises individually biasable gas-tight electrodes, the at least one electrode of the exit capillary comprises a surface coated with dielectric films. In some embodiments, the at least one sectioned radio-frequency multipole ion guide comprise a sectioned radio-frequency octopole ion guide followed by a sectioned radio frequency quadrupole ion guide. In some embodiments, the ion source comprises an ion mobility cell. In some embodiments, the apparatus further comprises an electron source fluidly coupled to the exit orifice and to the detector. In some embodiments wherein the apparatus further comprises an electron source fluidly coupled to the exit orifice and to the detector, the electron source is a pulsed electron source, a continuous electron source, or a combination thereof. In some embodiments, the apparatus further comprises a mirror assembly between the exit orifice and the detector. In some embodiments wherein the apparatus further comprises a mirror assembly between the exit orifice and the detector, the mirror assembly comprises a parabolic mirror or a cylindrical mirror; and, a flat mirror.

In one embodiment of the present invention, there is a method of analyzing gaseous ions, neutral species or mixtures of ions and neutral species comprising: introducing the ions and/or neutral species into a gas flow formation region to form a gas flow of the ions and/or neutral species, the gas flow formation region comprising a sectioned capillary having at least two electrodes; introducing the gas flow of ions and/or neutral species into at least one sectioned radio-frequency multipole ion guide, the sectioned ion guide comprising a plurality of electrically isolated electrode sections; applying voltage selected from the group consisting of DC voltages, AC voltage, RF voltages, and any combination thereof, to one or more sections of the at least one sectioned radio-frequency multipole ion guide; detecting the gas flow of ions and/or neutral species. In some embodiments, the method further comprises the step of varying one or more of the voltage selected from the group consisting of DC voltages, AC voltage, RF voltages, and any combination thereof. In some embodiments, the step of applying voltage to the ion guide comprises producing a resonant rotating field which extracts specific ions from the gas flow and causes the specific ions to follow a rotational orbit around the central axis of the multipole ion guide. In some embodiments wherein the step of applying voltage to the ion guide comprises producing a resonant rotating field which extracts specific ions from the gas flow and causes the specific ions to follow a rotational orbit around the central axis of the multipole ion guide, the resonant rotating field voltages are formed by applying an alternating current harmonic voltage with a phase shift of $\pi/2$ between adjacent rods within said radio-frequency multipole ion guide. In some embodiments wherein the step of applying voltage to the ion guide comprises producing a resonant rotating field which extracts specific ions from the gas flow and causes the specific ions to follow a rotational orbit around the central axis of the multipole ion guide, the step of applying voltage to said ion guide further comprises producing a gradient DC field which traps the ions following a rotational orbit in a region of the ion guide. In some embodiments wherein the step of applying voltage to said ion guide further comprises producing a gradient DC field which traps the ions following a rotational orbit in a region of the ion guide, the step of applying voltage extracts and traps ions of one or more m/z values and ion mobility cross-sections. In some embodiments wherein the step of applying voltage to the ion guide comprises producing a resonant rotating field which extracts specific ions from the gas flow and causes the specific ions to follow a rotational orbit around the central axis of the multipole ion guide, the resonant rotating field voltage is a graded resonant rotating field voltage. In some embodiments, the step of applying voltage to the ion guide comprises holding specific ions in the gas flow. In some embodiments, the step of introducing the ions and/or neutral species into a gas flow formation region comprises introducing the ions and/or neutral species into a supersonic gas flow. In some embodiments wherein the step of introducing the ions and/or neutral species into a gas flow formation region comprises introducing the ions and/or neutral species into a supersonic gas flow, the step of applying voltage to the ion guide comprises trapping ions in the supersonic gas flow. In some embodiments wherein the step of applying voltage to the ion guide comprises trapping ions in the supersonic gas flow, the step of introducing said ions and/or neutral species into a gas flow formation region comprises adding an admixture gas. In some embodiments having an admixture gas, the admixture gas comprises Ar and/or Xe. In some embodiments having an admixture gas, the step of adding an admixture gas fragments the trapped ions to create daughter ions of the trapped ions. In some embodiments wherein the step of adding an admixture gas fragments the trapped ions to create daughter ions of the trapped ions, the step of applying voltage selected from the group consisting of DC voltages, AC voltage, RF voltages, and any combination thereof, to one or more sections of said at least one sectioned radio-frequency multipole ion guide, extracts daughter ions from the gas stream. In some embodiments of the method wherein daughter ions are extracted from the gas stream, the method further comprises varying the voltage selected from the group consisting of DC voltages, AC voltage, RF voltages, and any combination thereof to reintroduce the daughter ions into the gas stream. In some embodiments, the method further comprises applying a DC voltage between the last electrode of the sectioned capillary and the first electrode section of the radio-frequency multipole ion guide. In some embodiments wherein the method further comprises applying a DC voltage between the last electrode of the sectioned capillary and the first electrode section of the radio-frequency multipole ion guide, the DC voltage between the last electrode of the sectioned capillary and the first electrode section of the radio-frequency multipole ion guide is applied when a desired ion is present in a region between the sectioned capillary and the radio-frequency multipole ion guide. In some embodiments wherein the DC voltage between the last electrode of the sectioned capillary and the first electrode section of the radio-frequency multipole ion guide is applied when a desired ion is present in a region between the sectioned capillary and the radio-frequency multipole ion guide, the method further comprises the step of removing the DC voltage between the last electrode of the sectioned capillary and the first electrode section of the radio-frequency multipole ion guide. In some embodiments wherein the method further comprises the step of removing the DC voltage between the last electrode of the sectioned capillary and the first electrode section of the radio-frequency multipole ion guide, the steps of applying and removing the DC voltage between the last electrode of the sectioned capillary and the first electrode section of the radio-frequency multipole ion guide are repeated one or more times. In some embodiments wherein daughter ions are extracted from the gas stream, the method further comprises the step of removing the voltage selected from the group consisting of DC voltages, AC voltage, RF voltages, and any combination thereof, to one or more sections of the at least one sectioned radio-frequency multipole ion guide. In some embodiments, the method further comprises the steps of applying a decreasing electric field in the direction of the gas flow in the radio-frequency multipole ion guide and measuring the mobility cross-section of the ions In some embodiments of the method, the step of detecting comprises detecting with a mass spectrometer. In some embodiments wherein the step of detecting comprises detecting with a mass spectrometer, the mass spectrometer is an orthogonal time-of-flight mass spectrometer. In some embodiments wherein the step of detecting uses an orthogonal time-of-flight mass spectrometer, the orthogonal time-of-flight mass spectrometer comprises a position sensitive multi-anode detector. In some embodiments wherein the step of detecting uses an orthogonal time-of-flight mass spectrometer, the orthogonal time-of-flight mass spectrometer is a bipolar time-of-flight mass spectrometer. In some embodiments, the method further comprises the step of passing the gas flow of ions and/or neutral species into a mirror assembly. In some embodiments of the method, the mirror assembly comprises a parabolic mirror or a cylindrical mirror; and, a flat mirror. In some embodiments, the method further comprises the step of impacting the gas flow of ions and/or neutral species with electrons from an electron source or with photons from a laser source.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
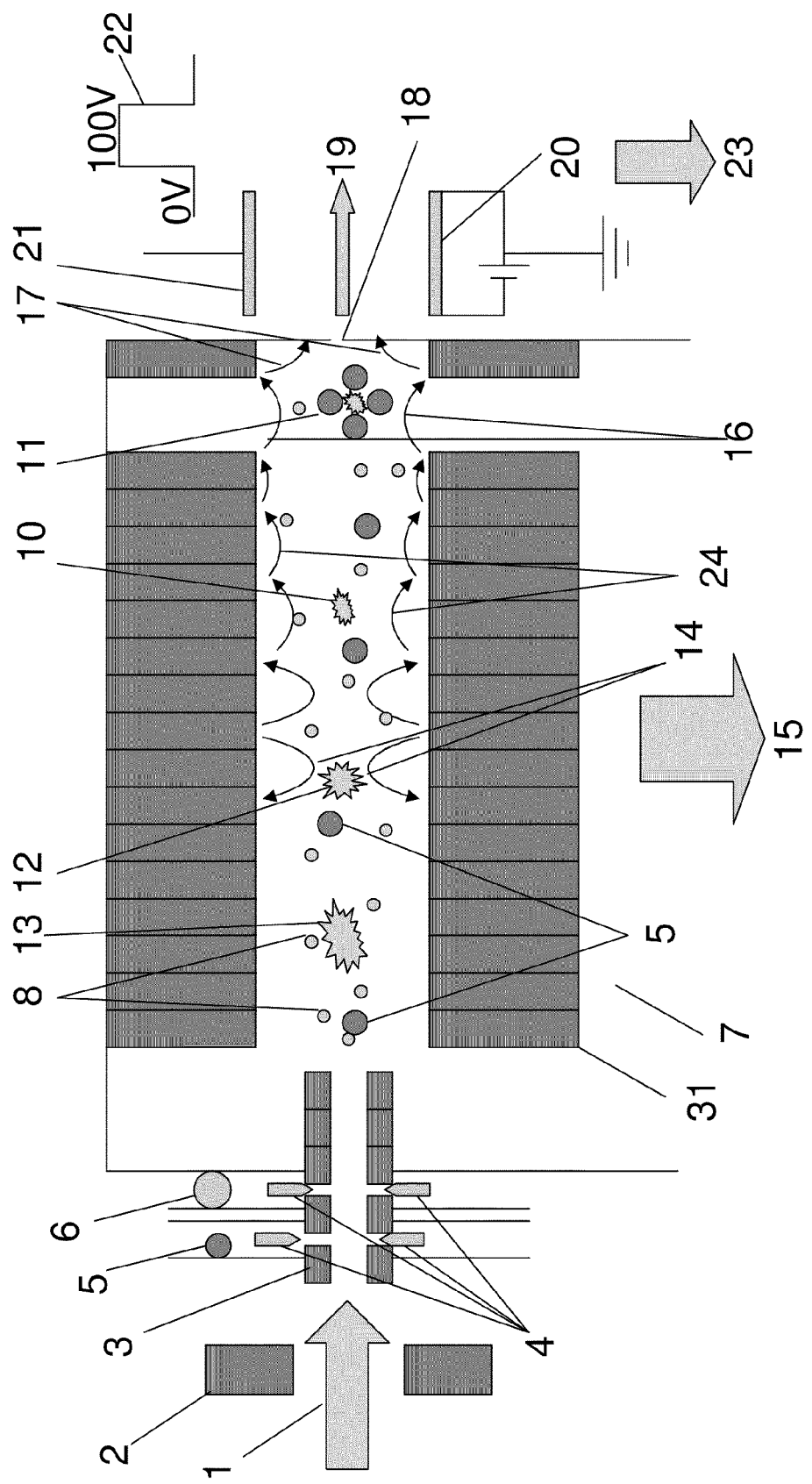
FIG. 1. Schematic diagram of the proposed RFQ interface between a mobility cell and an oTOFMS. Methods of trapping of ions with given value of mobility and their heating by the flow of heavier gas atoms are illustrated. Formation of ion clusters in supersonic gas flow and their controlled decomposition are shown too.

As used herein, "a" or "an" means one or more. Unless otherwise indicated, the singular contains the plural and the plural contains the singular.

As used herein, an "Radio Frequency (RF) Ion Guide" is a distinct group or cluster of several electrodes (rods) located around straight channel of ion transport with RF potential differences applied between adjacent pairs of these rods. In case the number of these rods is four RF-ion guide is called Radio-Frequency Quadrupole (RFQ) ion guide. RFM refers to Radio-Frequency Mulitpole one example of which contains eight rods and is called a RF-octapole.

RFM-ion guides as used in this application are built by segmenting each rod of the RFM into discrete electrode sections so that different DC voltages, and/or AC (RF) voltages can be applied separately or in any combination to cool, trap, and/or rotate ions along or around the gas filled longitudinal axis of the RFM and providing of the desired composition of supersonic gas flow along it axis may be used for trapping of some types of the ions, isolating of the desired ions from the trapped ones, their transformation and delivering of the products of these transformations to downstream instruments and devices.

As used herein, IM or a "mobility cell" or "ion mobility cell" is defined as a single or multi-channel device which performs mobility separation of ions.

As used herein "exit tube" or "exit capillary" is a segmented section of electrodes each of which electrode segment is individually electrically biased and each of which electrode segment has a diameter less than a preceding electrode diameter within the IM cell to which it is fluidly coupled, said "exit tube" or "exit capillary" being used allow differential pumping of the carrier gas exiting the IM cell before this gas can enter a TOFMS and where said exit tube in some cases is arranged to produce an adiabatic supersonic gas flow.

As used herein, "MALDI" means matrix assisted laser desorption ionization.

As used herein, "SIMS" means secondary ion mass spectrometry.

As used herein, "FAB" means fast atom bombardment mass spectrometry.

As used herein, the term "TOFMS" is defined as a time-of-flight mass spectrometer both linear or reflectron type; as used herein, "oTOFMS" is defined as a time-of-flight mass spectrometer both linear or reflectron type configured orthogonally to the analytical axis of a preceding instrumental platform such as, for example, the separation axis of an ion mobility cell; "LoTOFMS" is defined as linear oTOFMS.

As used herein IM-oTOFMS refers to a combination of an Ion mobility spectrometer with an orthogonal time of flight mass spectrometer.

The present invention relates generally to instrumentation and methodology for characterization of chemical samples based on ion mobility spectrometry (IMS) and mass spectrometry (MS). Specifically, the invention relates to improved IMS, using the concepts of a new type of interfacing of ion mobility cells with an orthogonal injection time-of-flight mass spectrometer (TOFMS) based on significant interface cooling of the ion beam by combining an adiabatic supersonic gas flow with a focusing radio-frequency quadrupole (RFQ) or multipole (RFM) ion guide. The improvements also include the capability to initiate chemical transformations within separated or isolated ions under high or low temperature conditions via their collisions with atoms, molecules and clusters which are either present or have been intentionally introduced and/or which were intentionally formed within the adiabatic gas flow. Structural and conformational information about the separated isolated ions can be obtained over a wide temperature region ranging from close to absolute zero up to the limit of the thermal stability of the isolated ions. Measurement of a variety of physical characteristics including primary and secondary structures (as well as the ratio of ion volume to charge) is now possible over this wide temperature range. Moreover, a new type of separation of biomolecules in the gas phase is described based on creating conditions in the neutral-ion reactor near the isoelectric point for the molecule of interest. Such possibilities are possible because of a new design of an ion mobility cell/TOFMS interface comprising a well collimated cooled gas flow, a means of controlling the gas phase composition and a unique RF-ion guide which provides controlled retarding and accelerating DC electric fields as well as an AC rotating field. An electron impact ionizer located after the RF-ion guide allows measurement and control of the composition and properties of the gas flow allows additional structural information about the ions and their products which are being manipulated inside the RF-ion guide. Additionally, the technique of multi-channel data recording provides kinetic and structural information. The present invention enables methods both for increasing the dynamic range of the measurements and for obtaining additional ion shape analysis beyond that available from ion mobility alone. These improvements may be used to increase the information content and the throughput of ions from a sample into downstream instruments. The resulting instruments and methods are useful for qualitative and/or quantitative chemical and biological analysis.

A new approach for isolation and subsequent rotation of ions in a gas filled RFM, is at the heart of this invention and is now described. It should be understood that while an RFQ is described for illustrative purposes, other RFMs (such as RF octopole, etc.) may be used. Analyte ions can be entrained in a narrowly divergent divergent gas beam created (for example) in a capillary interface between an ion mobility cell and a mass spectrometer said gas beam being formed during the expansion of the mobility carrier gas from high pressure to low pressure. If at the point just after the gas expansion (where the gas beam is narrowest) the entrained ions are then pulled from this gas beam by a momentary electric or magnetic force into a quadrupolar (or multipole) region, then these ejected ions may be made to rotate in a gas density which is almost that of the residual gas in the interface and is several orders of magnitude less than the pressure within the cooled beam from which the ions originated. Thus, ion rotation may take place in a spatial region of almost constant residual gas pressure outside of and around the dense gas beam which is diverging along and around the central (longitudinal) axis of the RFM. It is thus possible to trap and purify parent ions and, if desired, further manipulate these purified ions (fragmentation, gas phase ion/molecule reaction, electron attachement) followed by subsequent reinsertion of the purified parent ions or their reaction products into the neutral gas beam for further manipulation and transport either to an MS or to other traps or into additional IM cells or combinations thereof. There are some substantial advantages to identifying and manipulating ions (particularly IM separated ions) by rotating the ions in a constant residual gas pressure when compared to traditional RF traps and cooling devices wherein ions are made to oscillate in and out of the gas beam (as in the conventional motion within a quadrupole). The stable orbit of an ion in a gas-filled rotating field region is determined both by its ion mobility crosssection and its mass/charge ratio. Thus, the coupling of such a rotating field ion trap is particularly useful at the end of a mobility cell which injects ions into the rotating region which have been pre-selected by their IM cross-section. Simple theoretical considerations, confirmed by computer simulations and experimental measurements, allow the following main expressions which describe the properties of ion rotation within a constant gas density.

The resonant rotation angular frequency $\hat{\omega}_{rot}$ for given ion charge ze (e is an elementary charge), mass m, RF-voltage amplitude $V_{rf}$, internal radius of RFQ $r_0$ and angular frequency of RF-voltage $\omega$ for small enough gas density (valid for the cases under consideration) is given by:

$$\hat{\omega}_{rot} = \sqrt{2}\,\frac{zeV_{rf}}{mr_0^2\omega}. \quad (1)$$

The resonant rotating radius for a given m/z value is proportional to the mobility value K for given ion and amplitude of rotating voltage $V_{rot}$:

$$r_{res} = \frac{Kmr_0 V_{rot}\omega}{zeV_{rf}\sqrt{2}}.$$

The value $$\frac{Km}{ze} = \tau_v$$

is a relaxation velocity time for the given ion at a particular gas density as described in the following section. $2\tau_v$ is a characteristic time for achieving a steady state rotation of ions. The radii of rotation for other ions with different m/z values (and the same mobility) should follow a bell shaped peak (close to Lorentzian in character) with relative width at half height given by:

$$\frac{\Delta(m/z)}{m/z} = \frac{2\sqrt{2}}{\tau_v q_M \omega},$$

where the Mathieu parameter $$q_M = 4\frac{zeV_{rf}}{mr_0^2\omega^2}$$

should not be more than 0.7 for stable motion of a given ion. Thus the maximum possible resolving power for rotational excitation $$R_{rot} = \frac{m/z}{\Delta(m/z)}$$

is given by:

$$R_{rot} \leq 0.247\tau_v\omega.$$

The relaxation velocity time may be estimated through average collision frequency v and consequently through collision cross section $\sigma$, gas density n, and average thermal velocity $\overline{V}$ of the carrier gas atoms and their mass M:

$$\tau_v \approx \frac{m}{Mv} = \frac{m}{Mn\sigma\overline{V}}.$$

An example calculation of $R_{rot}$ can be estimated for the following experimental conditions: For an analyte mass m=1000 Da, carrier gas He M=4 Da, n=3.5×10$^{13}$ for 1 mTorr residual He gas pressure, $\sigma$=3×10$^{-14}$ cm$^2$ (crosssection of analyte in He), and an average velocity of helium atoms for room temperature $\overline{V}$=126000 cm/sec we obtain $\tau_v\approx$1.9 msec, and for the angular frequency $\omega$=2$\pi$·2 MHz $R_{rot}\leq$5800. For larger frequencies and also larger RF voltages (or less gas density) the resolving power would be even greater. The resolving power for larger ions should also increase as a function of m/z since the mass of the ions is expected to grow faster than their collision cross section. Thus, the method of ion rotation has significant advantages for structural determinations of IM separated ions since other approaches to ion purification and excitation move the analyte ions for some time near the dense gas flow axis thus severely limiting their resolving power. However, there are factors which limit the resolving power of the rotational method. Equation (1) which gives the resonant rotating frequency shows that a variation in $r_0^2$ (the squared internal RFM radius) may control the resolving power if the manufacturing precision of the RFM is not good. Also, additional voltages, if improperly applied to some RFQ sections for the retardation or acceleration of ions out of the gas stream and for trapping of the ions may also result in some losses of rotational resolving power. There are two important rules to follow when applying such voltages. The first one is that a uniform electric field along the RFM satisfies the Laplace equation by having a zero component in the orthogonal plane. Thus this field will not have an influence on the ion rotation. The second favorable situation is a linear increase or decrease of the electric field along the RFQ axis. Such fields would change the rotating frequency of the ions but would not change the character of harmonic motion of ions (on average). Thus in such an ideal case the resolving power would not change noticeably especially if this field is not very strong. Therefore the use of such fields for trapping rotating ions is quite feasible. It is interesting to note that AC harmonic fields with a linearly changing amplitude directed along RFQ axis also do not change (on average) the harmonic character of ion motion. The reason for that is the known quadratic dependence of the effective potential of a harmonic AC field on its amplitude (this property was described for the first time (to our knowledge) in the book "Mechanika" by Landau and Lifshitz published in Russia in the mid 1950's in which Petr Kapitsa, described the idea of such influences of fast field oscillations. In our case the amplitude can be changed linearly. After estimating the effective force by first calculating the gradient a linearly changing force would be present along the axis and in the orthogonal plane too. The only difference when compared to a DC field alone is that the force in the orthogonal plane is always a focusing force. The main restriction for the possible number of rotating ions of given m/z value and mobility is the space charge influence. As rotating ions with different m/z and/or mobility values are located at each time in different locations inside the RFM their mutual space charge influence simple calculations suggest that the accumulation of 1 000 000 or more rotating single charged ions over wide range of m/z and mobility values may be possible within a linear RFM of 10 cm length. In analogy to the situation for the usual application of RF ion traps, the combination of several harmonic rotating fields along the linear RFM should independently excite ion motion at different locations along the RFM.

The present invention deals with systems and methods using ion mobility drift cells for transporting ions through a high pressure gas to a TOFMS. The following concepts are described in various embodiments of the present invention: (a) controllable production of chemical transformations of separated or isolated ions under high or low temperature conditions via their collisions with atoms, molecules and clusters included or formed inside adiabatic gas flow, (b) extracting information about primary, secondary structures and the spatial shape of the ions over a wide range of temperatures from the close to absolute zero up to the temperature defined by the limit of thermal stability of the ions, (c) multichannel data recording which is essential for obtained kinetic data processing and which allows also to increase the efficiency of sample use by obtaining as much useful information as possible about the sample in a reasonably short time, and (d) a new type of separation of biomolecules in gas phase based on providing conditions in neutral-ion reactor close to the isoelectric point for the molecule of interest. Specifically, the improvements lie in (i) use of a new design mobility cell/TOFMS interface comprising well-collimated supersonic gas flow and an original RF-ion guide which has the capability of creating controlled DC and additional RF electric fields combined with an AC rotating field (ii) controlled variation of the buffer gas composition inside the RF-ion guide by providing controlled amounts of larger reagent gas admixtures to the main ion mobility carrier gas (carrier gas is usually helium for the most of applications), (iii) accelerating, retarding or trapping of target ion(s) by appropriate DC and/or RF axial fields and AC rotating field inside RF-ion guide, (iv) removing undesired trapped or moving ions by resonant rotating field, (v) high selective isolation of ions with a desired m/z and mobility values by joint influence of resonant rotating field, DC fields and supersonic gas flow, (vi) controlled heating of ions by intentionally adding admixtures of relatively heavy atoms to the carrier gas flow (Ar for example when added into a He flow will have ten times more energy than He atoms), (vii) single collision induced dissociation of desired ions by addition of a controlled amount of significantly larger atoms such as Xe to the carrier gas flow, (viii) performing different chemical transformations of ions for a given temperature and time such as cluster formation, H/D exchange, ion molecule reaction, noncovalent complex formation by addition to the carrier gas flow of corresponding reagents, (ix) use of electron bombardment ionization of the combined gas flows for estimation of the gas flow parameters, for purity control of gases and for composition control of their mixtures as well as for ionization of neutrals (which are usually not measured as reaction products during the ion transformations), (x) by changing the kinetic energy of electrons it is possible either to produce electron attachment dissociation of ions and/or to record ion appearance curves as a function of electron kinetic energy for dissociation of different bonds in the ions which may give estimations for local electric field in the ion by comparison with kinetic data for thermal decomposition of the same bonds (xi) direct measurements of isolated ion collision cross section over a controlled temperature range from near absolute zero up to high temperatures (close to the dissociation temperature for the ion), (xii) adjusting the composition of the gas flow to provide conditions in the neutral-ion reactor close to the isoelectric point for the molecule or species of interest and performing on that basis a new type of gas phase separation of biomolecules, and (xiii) use of a unique bipolar time-of-flight mass spectrometer which is able to simultaneous record both positive and negative ions and coincidences between them. Steps (iii)-(viii) may be repeated the desired number of times to isolate and manipulate (e.g. fragment) selected ions. Thus the method includes the new possibility of $MS^n$ of primary and product ions which have been selected at each step both on the basis of ion mobility cross-section and m/z (with moderate to high resolving power).

In comparison to conventional methods of temperature programmed collision induced dissociation, the improvement described in (vi) above provides a significantly more precise yet simple procedure for establishing the desired temperature of the selected ions which in turn improves the accuracy of kinetic measurements. Likewise, the new method of ion decomposition described in (vii) above is more effective for dissociation of desired bonds in the ions as it relies on randomly distributed single collisions to heat ions to a chosen temperature. This procedure selectively cleaves the weaker chemical bonds in the chosen ion. Product ions with a smaller ratio of charge to collision cross section than the isolated parent ions would be relatively immune from decomposition. Since the smaller product ions would be able to overcome the potential barrier retarding the isolated ions they would exit the spatial regions where the parent ions are being heated and decomposed since their velocity would gradually increase to the velocity of the gas flow. If a further investigation of these product ions is desired (such as subsequent decomposition for MS$^2$) they can be isolated from the heating procedure before they are decomposed and stored for further use by putting a stronger retarding potential at some distance from the first retarding field which was (used to isolate the parents) so that a "shifting" field is created between the corresponding opposite sections of RFQ-RFM rods. This shifting field removes and conserves the product (daughter) ions during the time necessary to complete the decomposition or transformation of the desired isolated parent ions before the daughters ions are further decompose in the heated region of the gas flow. Likewise, ion products with larger values of charge-to-collision cross section ratio than the parent would move from the position where they were created as the trapped parent ions is being decomposed or reacted with a neutral gas to a position where the force of the electric field on these product ions is compensated by the gas flow. Therefore, for product ions of larger cross-section than the parent a second "shifting" field can be created in the opposite direction which would also remove these ions from the flow axis so that they too would not be heated and decomposed further. These two opposite fields located at both sides of the region in which the parent ions are isolated will not significantly change the location of the parent ions so their heating and transformation (e.g. fragmentation) may be continued. Some of the very small product ions may come to the rods and be lost, but usually sufficient structural information about large parent ion species such as biopolymers may be obtained from product ions not much less than half of the m/z of the parent ions. Improvements (viii) and (xi) provide a unique method for the measurements over an unprecedented temperature interval—from the region close to absolute zero to the values up to and exceeding where ion decomposition can occur—which is difficult or impossible to do by other methods. Furthermore, trapping ions of a given mobility and/or a given m/z value can be accomplished with considerably reduced restriction from space-charge compared to existing conventional methods since ions are trapped only for a narrow interval of mobility and/or m/z values. This feature has implications not only for analysis, but perhaps as importantly for preparatory scale purification and selected area deposition of mobility and m/z selected molecules. Moreover, isolation and storage of a variety of desired ions by this new method does not necessitate the loss of other larger or smaller ions as is mandatory with other trapping methods. We pick certain desired ions out of the gas stream while retaining the others within the gas stream which forces their transport either to a mass spectrometer for analysis or to other RFM traps in series for further refinement.

There are at least four possible methods of isolation of desired ions which may be chosen given the demands of specific experimental situations. 1) The simplest method removes undesired ions from the trapped desired ions with a resonant rotating field determined for a specific chosen interval of ion mobility. This method demands only the knowledge of m/z of trapped ions and gaseous conditions in the region of trapping. Here undesired ions are removed from the trapped ones and thus this method is similar in result to other methods of isolation of desired ions within a trap. The time for ion removing for some set of m/z values may be large enough or demand using of more complicated power supply for providing sums of rotating fields with given set of frequencies instead of device for producing of a single harmonic rotating field. 2) Alternatively, it is possible to excite the rotation of desired ions in a way which shifts them into a stable orbit within a region of reduced residual gas pressure around the main gas flow. This allows the undesired trapped ions which remain behind in the gas flow to be transported by this gas flow to a serial RFM or directly into a mass spectrometer by reduction of the retarding trapping potential. Once the desired ions flow away, subsequently reapplying the retarding trapping voltage while simultaneously stopping the rotating field will re-introduce the desired ions back into their trapped position within the gas stream where they would be ready for further manipulation or transformations. Here no ions are lost for measurements. To implement this method it is necessary to know the pressure gradients within the RFM, the m/z value, and the mobility coefficient (collision cross section) of these desired ions. The ion mobility is already give by the retention time within the ion mobility separation which is used. Both approaches (1 and 2) may be time consuming and inconvenient for classic mobility separation of ions when mobility peaks are relatively short in time and resulting mobility/mass spectra are accumulated by summing mobility separated ions over a repeated number of introduction of sample ions into the ion-mobility mass spectrometer. Thus, it may sometimes be undesirable to repeatedly perform the procedures of ion trapping, isolation and transformation after each and every each sample ion introduction. 3) For continuously trapping specific desired (target) ions from the sample of ions which are being repetitively introduced into the IM-TOFMS, it is possible to continuously maintain the resonant rotating field throughout the acquisition time of the experiment. In this case only ions with chosen m/z value would come out of the main stream of the gas flow and would move along RFQ-RFM ion guide very slowly and independently of the other ions remaining in the gas flow. Providing a small accelerating field at the beginning of the guide followed at some distance along the RFQ-RFM axis by a retarding potential which is weak enough not stop any ions within the on-axis dense gas flow while continuously applying an appropriate rotational field around the RFQ axis in the region between these two fields will lock the desired ions in a rotational orbit outside the gas stream and between the two fields. 4) Alternatively it is possible to trap ions within a resonant rotational excitation as the ions with desired mobility are entering the RF-ion guide. A retarding potential should be applied at all times except when the desired ions move into the beginning of the ion guide. This retarding potential will prevent ions from drifting outside the main gas stream and force their motion inside the stream at the beginning of the ion guide. Just as the desired ions enter the RFQ the polarity of the retarding potential changes is reverse which moves desired ions out of the flow into a region influenced by a weak rotating field which is effective only in the residual gas pressure outside the main stream gas flow. After the time for extracting of the desired ions has passed, the rotating ions are shifted by application of potential gradients from the beginning of the ion guide and trapped between two opposed retarding potentials further along the RFQ axis.

Finally, a new type of ion separation and isolation, not normally possible with mass spectrometry, results when conditions within the gas flow are created close to the isoelectric point for the selected molecules in the gas flow. This approach is described in detail herein. Furthermore this type of biomolecule separation will simultaneously present both positive and negative ions to the mass spectrometer; therefore, a new scheme for bipolar time-of-flight mass spectrometer which is able to simultaneous record both positive and negative ions (and coincidences between these positive and negative ions) is essential for gaining maximum information from the new separations. This new mass spectrometer and its coupling to the newly enabled separation methods is also described herein.

These improvements may be used to increase throughput from an ion source to downstream instruments and they may also provide additional information about the samples. The resulting instruments and methods are useful for qualitative and/or quantitative chemical and biological analysis.

In the present invention ions of interest are isolated using both their mobility and m/z values. Isolation of the desired molecules on the basis of their ability to form different ionic forms under controlled conditions in the gas phase which, in conjunction with significantly improved control of the experimental reaction parameters determining the specific ion transformations, gives an opportunity for measuring unique structural information about ions present in the original samples.

When ion mobility cells, filled with a few Torr of buffer gas, are used as a volume/charge separation stage in front of a mass spectrometer, the cooled ions exit through a small exit aperture or exit capillary into a differentially pumped low pressure region before entering the high vacuum region of the mass spectrometer. To minimize transmission losses through the small aperture, the ion beam inside the mobility cell must be focused. Ion beams should be as narrow as possible in the region between the mobility cell and TOFMS to allow the use of small differential pumping apertures (enabling lower gas flow) and to achieve higher mass resolution for TOFMS operation. Therefore the beam should be cooled as much as possible to obtain low divergence. As described in co-pending U.S. patent application Ser. No. 11/441,766 filed May 26, 2006, (Multi-Beam Ion Mobility Time-of-Flight Mass Spectrometry with Multi-Channel Data Recording) cooling can be done by directing a gas flow containing mobility separated ions through a narrow exit tube (or tubes for multi-beam systems) which separate the high pressure ion mobility region from the differential pumping region prior to the mass spectrometer. By such a procedure, the gas and ion stream case can emerge with an angular divergence corresponding to a temperature of 1K or less and the ion beam traveling in such an adiabatic supersonic gas flow can be further focused to even smaller final diameters by the use of an RF-ion guide as suggested in U.S. patent application Ser. No. 11/441,766, filed May 26, 2006.

FIG. 1 shows the improvements of this interface region over the prior art by making an the RF-ion guide wherein the rods of the RFM contain multiple electrically isolated sections so that it is possible to create any combination of variable DC and AC fields inside the RF-ion guide. These fields may be arranged as will be described herein in order for trapping and isolation of selected ions and for transforming these isolated trapped ions by collisions with some admixture gases added to the buffer gas flow. This approach of trapping and transforming may be used in structural investigations of samples of different nature. The transformation of the trapped ions may include fragmentation as a special case, but will also include a variety of different ion-molecule and or ion-ion gas phase reactions. Two properties of the RF-ion guide shown in FIG. 1 should be noted: A) there exists a large difference in gas density exists along the center axis of the RFM within the directed gas flow compared to the residual gas density in the region radially outward from the RFQ axis; therefore, small electric fields can have a strong influence on ions outside of the main gas stream yet will not significantly disturb the motion of ions which remain inside the gas flow along the RFM axis, and B) small admixtures of heavier atoms (5,6) and molecules intentionally combined with the main carrier gas flow (usually helium (8)) will not significantly change the gas flow velocity and the temperature of this carrier gas (8). After some distance along the RFM axis after the last electrode (61) of the exit capillary, these heavier admixtures (5) will have attained the same drift velocity as the lighter buffer gas flow (8). Therefore, this means that heavy admixture gases have less divergence (by a factor equal to the square root of the ratio of their masses) than the buffer gas (e.g. helium buffer gas). Thus, the heavy gas density relative to the density of the lighter buffer gas would increase as their distance from the exit tube increased. The density of heavy admixture atoms (or molecules) along the axis of the flow approaches a limit which is equal to the product of initial admixture relative density and the ratio of its atomic (or molecular) mass to the mass of the main gas atoms. For example for Ar (5) admixture atoms in He (8) this factor of increasing relative density along the axis of the flow would be 10. During and after the expansion the admixture (atoms) rapidly acquire the average velocity of the predominate helium buffer gas atoms; therefore, the admixture atoms energy of motion is more than that of helium atoms by the ratio of their masses. Thus, if an ion (12) exiting from the IM cell (or any other ion source) into the RF guide is intentionally stopped or retarded near the flow axis (in a region of high relative admixture density) within this combined He (8) buffer and argon (5) admixture gas flow then this retarded ion (12) may be effectively heated by collisions with these heavier admixture atoms (5); furthermore, the temperature of this heating is not expected to be as dependent on the chemical and structural characteristics of the ions when compared to a more traditional method of ion heating which occurs, for example, in CID (collision induced dissociation). In traditionally applied CID, ions are decomposed by moving them within a gas under the influence of a variable electric field and variable gas density CID entails a wide variety of center of mass collision energies between the ion and the inert gas). Beginning at a distance along the flow axis (which is far enough from the tube exit to ensure that the admixture atoms and the entrained ions have come to equilibrium velocity with the He) the temperature of this ion heating will depend with good accuracy only on the relative velocity of ions and the gas flow. Shifting of ions and their dissociation product ions away from the gas flow axis would reduce this temperature only slightly proportional to the damping of a narrow Gaussian density distribution of the larger atoms or molecules.

In FIG. 1 an IM cell (2) is fluidly coupled to a gas dynamic interface (7) by an exit capillary (3) comprising gas tight individually electrically isolated and biasable electrodes (61). The cross section shown in (FIG. 1) of the gas dynamic interface (7) comprises an RFQ (300) (two rods of which are shown schematically in cross section each constructed by 16 independently biaseable electrode sections (30)). The interface (7) provides for differential pumping (15) and for processing and forming an ion beam (19) for ultimate injection into a detector. This detector can be a oTOFMS with multi-channel data recording which is used for different embodiments for analysis of ions of both signs directly produced by ion sources or after post-ionization of neutrals within the trapping region as is described, for example, in co-pending U.S. patent application Ser. No. 11/441,766, filed May 26, 2006 entitled "Multi-Beam Ion Mobility Time-of-Flight Mass Spectrometry with Multi-Channel Data Recording" and U.S. patent application Ser. No. 11/441,768 filed May 26, 2006 entitled "Multi-Beam Ion Mobility Time-of-Flight Mass Spectrometer with Bipolar Ion Extraction and Zwitterion Detection". Ions entrained within a gas flow (1) (normally helium) are directed from the IM cell (2) into a sectioned exit capillary (3) where adiabatic supersonic gas flow is formed and ions move under the combined influence of accelerating gas flow and electric fields along the tube (3) provided by biasing to the individual capillary electrode elements (61) (five electrodes (61) are illustrated in FIG. 1). Preferably, the surfaces of the electrode sections inside this tube should be coated with thin dielectric films and charged before the experiment by charges of the same sign to reflect ions from the walls or may be fabricated from a piezoelectric device which can be biased to transmit ions of both signs. This capillary exit (3) has several valved (4) input orifices for inserting different gaseous admixtures (5,6) into the gas flow. The delivery valves (4) under computer control should provide the desired flows of these admixtures. As examples of these admixtures atoms of Ar (5) and Xe (6) are shown symbolically. The delivery valve for Ar (5) is shown open and other valves are closed. Obviously more than two valves each with its own special gas may be incorporated in this section. After the exit tube the supersonic gas flow containing both entrained ions and intentional admixtures is inserted into sectioned RFQ ion guide (300) equipped with sectioned multielectrode rods (30), and is pumped by differential pumping (15). In the ion guide (7), mobility separated ions (10), (12) and (13) are focused to the axis of the flow under influence of RF-voltage and gradually acquire the drift velocity and the temperature close to those of the gas flow. As mobility separated ions of interest enter the gas flow, different voltages (DC, AC and RF) can be individually or collectively applied to each of the electrically isolated sections of the RF-quadrupole rods (31). DC retarding voltages are intermittently applied at chosen times to electrode sections (31,37) of the bottom and top rods in the middle of the RFQ (300) so that a retarding field (14) is created which stops the ions with a medium mobility (12). The "small" ions (10) will have already passed this region and are not affected by this field while "large" ions (13) are able to overcome this retarding field due to the higher energy they obtain in the adiabatic expansion relative to the the medium sized ions (12) which are made stationary by the field. These stationary ions (12) may then be heated to a desired temperature by seeding argon atoms (5) into the carrier gas (e.g. He) gas flow (8) with a velocity close to 1400 m/sec (average quadratic velocity of helium for the room temperature ~300K). This corresponds to ~3000K for kinetic energy of the Ar atoms. Thus 10% admixture of Ar passing through and colliding with the stationary ions (12) would give about 600K of ion temperature. By variation of the Ar abundance in He, the desired temperature of the stationary ions may be achieved. To measure and control the ratio of Ar/He in the gas flow an electron impact ionizer with electron emissive cathode (20) and anode (21) is located just after exit orifice (18) of gas dynamic interface (7). The gas and ion flow (19) which is entering the oTOFMS is ionized by rectangular pulses of electrons created by applying a voltage (22) to the anode (21). The $He^+$ buffer gas and $Ar^+$ admixture ion intensity created by the electron impact ionization can be measured with the oTOFMS in the same process as IM separated ions (19) are being recorded so that the rare gas ion signals can be used to calibrated the concentrations of He and Ar gas in the gas beam which was used to process an manipulate the IM separated ions (19). A small area orifice (18) and adequate pumping (23) provides a low operational pressure inside the oTOFMS.

Another important phenomenon to be considered in a gas dynamic interface is the capability for formation of ion clusters (11) with admixture molecules at the end of the RFQ (300). To investigate formation and fragmentation of these clusters (11) (which may give additional information about ion conformation at low temperatures) electric fields (24) and (16) may be varied giving various intensity distributions of cluster ions. For the most accurate quantitative information about cluster formation, the resulting electric field distribution along gas flow axis should be proportional to the gas density to provide constant ion drift velocity and consequently constant temperature of the ions. This approach is described in more detail much later in this application. To increase transmission of these ions through exit orifice (18) additional short range electric field may be created (17).

Figure 2:
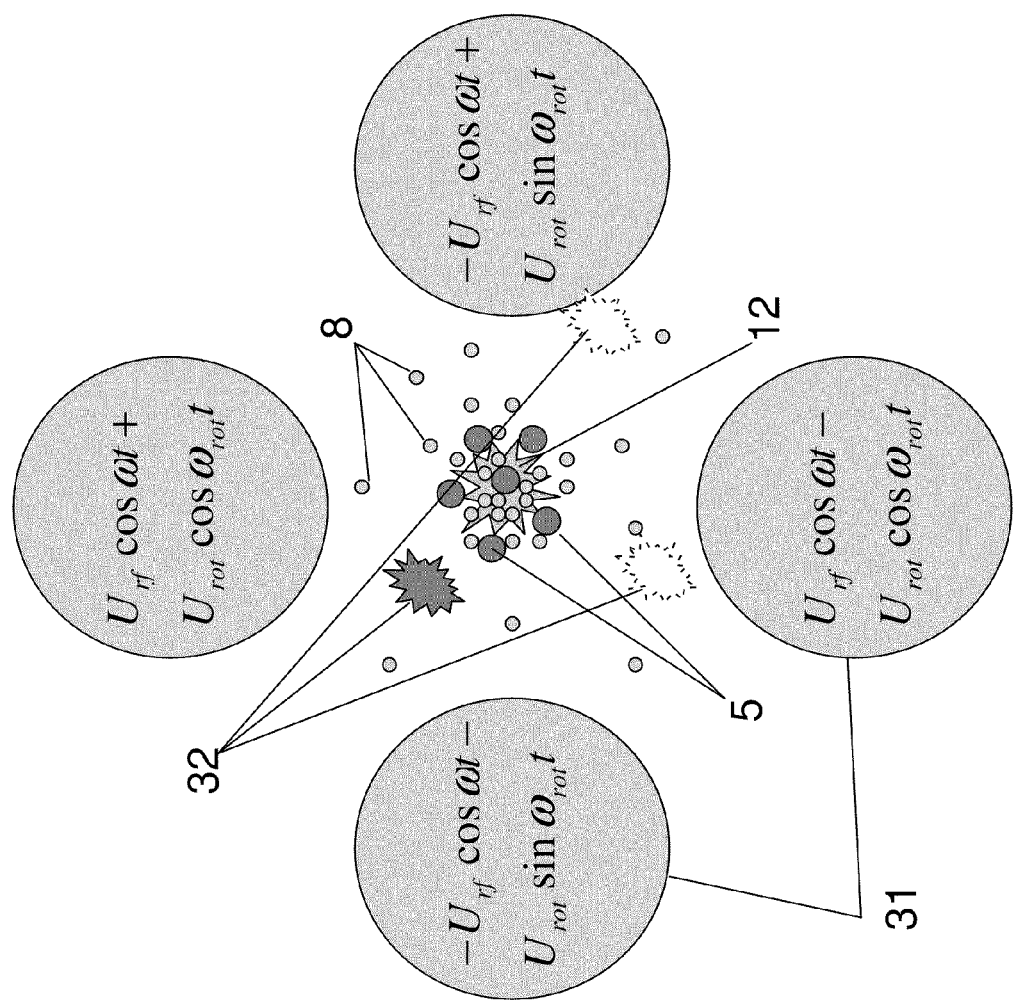
FIG. 2. Cross section of RFQ-ion guide (from FIG. 1) showing the applied focusing and rotation voltages. Excitation of rotational motion of selected taken ions from those trapped in the gas flow is shown. The rotational field may be used as for removing of undesired ions or alternatively for isolation of chosen ions for further transformations.

FIG. 2 is a cross section taken through electrodes 31 and 37 of FIG. 1 and shows how a rotating RF field can be applied in addition to the DC voltage and RF cooling voltage already applied on these electrodes. In one embodiment of the present invention, a resonant rotating field is used for removing undesired ions (32) from the trapped ions (12) as shown in FIG. 2. This field is created by applying an AC harmonic voltage with phase shift π/2 between adjacent rod segments (31), (34), (37), (36), within the RFQ (300). Our previous experience in using rotating fields for heating and decomposing ions (Raznikov, et. al., RCM, 15, 1912-1921, 2001) shows that a mass resolving power of a few hundred (FWHM) may be achieved for such a case as shown in FIG. 2 where the trapped ions remain in the dense gas flow. Further purification of the trapped ions (12) may be achieved by re-exciting ion rotation with some rotating frequency appropriate for the m/z of any undesired ions remaining in the trapping region.

Alternatively it is possible all at once to generate the rotating field as a sum of resonant rotating fields for ions with all undesired m/z values. It is possible to excite resonant rotation of just the desired ions from all the trapped ones instead of removing all ions but the desired. Thus the desired ion comes out of the gas flow and the undesired remain trapped. The amplitude of the rotating field in this case should provide enough displacement of the desired ions from the axis of the gas flow to maneuver them into a region out of the dense gas flow and into a region where the gas density is noticeably less than on the axis. This RF amplitude must be chosen carefully because if too large then the desired ions will rotate into the rods where they would be lost. If the RF amplitude is appropriate, ions will start to drift backward as they transition out of the main gas flow under the influence of retarding field and finally they would stop their drift as they are completely moved out of the gas flow and they would then rotate in a stable orbit around the gas flow. In the case of a weak retarding field which decreases slowly in the direction opposite to the gas flow, the location of the desired rotating ions may be removed upstream far enough from the trapping region (where the gas beam diameter is minimum) so that only undesired trapped ions are released when the retarding trapping potential is switched off for a time just sufficient for releasing the undesired ions but not the desired rotating ions. Switching off the rotating field after restoration of the retarding field would result in re-isolation of the purified desired ions back in the gas flow and in the trapping region where further manipulation and transformation of the purified ions could occur.

Figure 3:
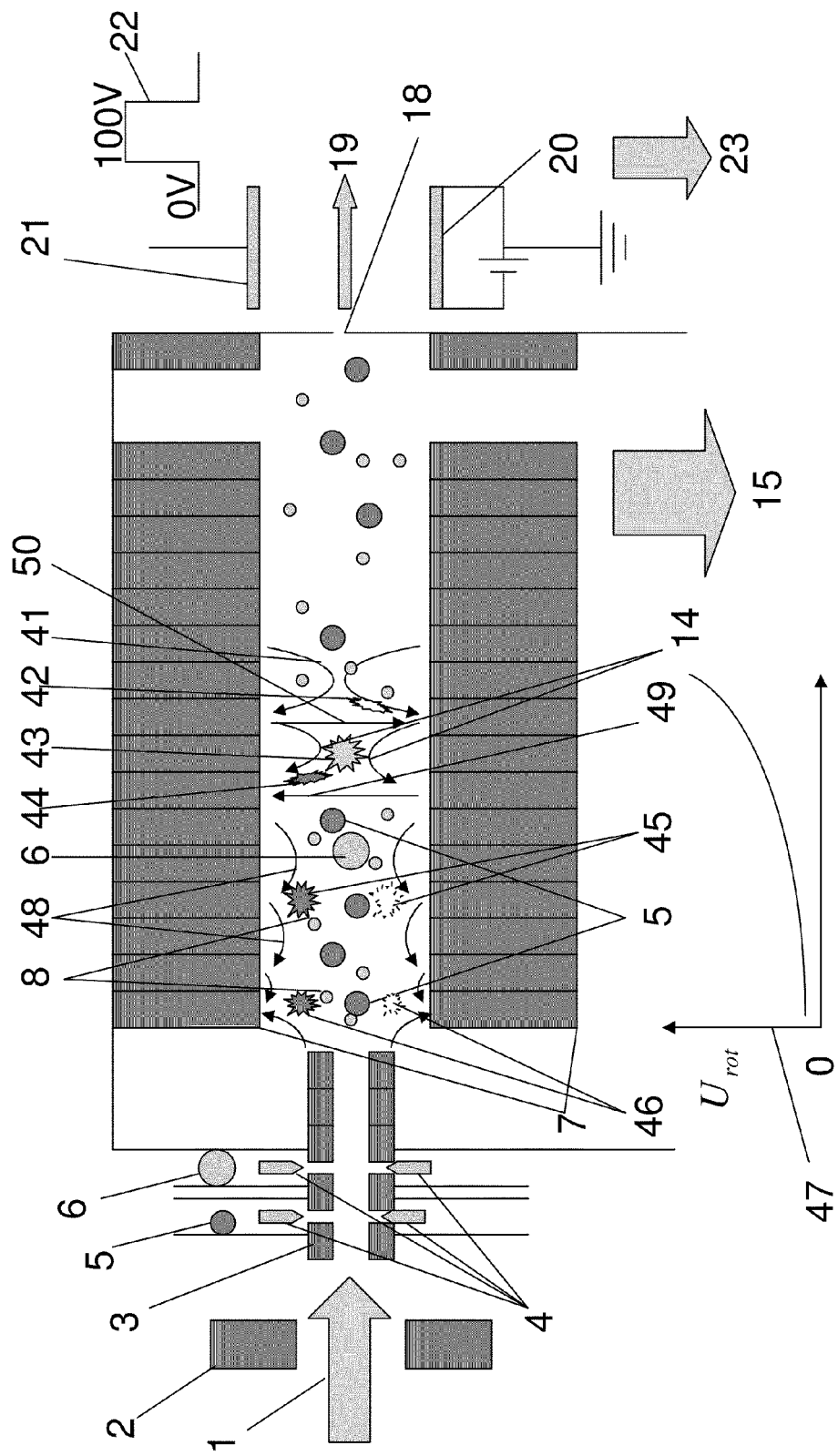
FIG. 3. Illustration of parent ion decomposition while removing product ions from the zone of decomposition and further isolating and purifying these desired product ions with resonant rotational fields.

After isolation of the desired ions (43) in a trapping region by the retarding fields (14) which are shown in FIG. 3 the ions may then be subjected to different transformations. For example, collision induced dissociation may be provoked by a single impact of relatively high energy large atoms (Xe)—(6). Ions (43) are heated by Ar (5) collisions to high enough temperature to be almost ready for the decomposition. If there is no desire to further isolate individual product ions for additional investigations then only RF focusing voltages are applied to the rods (7) of the RFQ. The "small" dissociation products (44) (with a collision cross section to charge ratio less then that for parent ions) will be removed from the flow axis under influence of the field (49) between opposite RFQ sections of rods; therefore, they would not be subjected to further decompositions by heavy admixture atoms which have significantly less divergence than that of the helium atoms. "Large" product ions (with a collision cross section to charge ratio more then that for the isolated parent ion) would overcome the retarding field (14). Under the influence of stronger retarding field (41) and the field (50) being opposite to the field (49) but created between the other sections of RFQ rods they (42) would be removed from the axis too. Thus, with the "large" and "small" product ions being continuously removed, the main dissociation mechanism is by single heavy atom (Xe) collisions with individual parent ions (which have been preheated near dissocation by previous Ar collisions). To isolate the ions with desired m/z value from the decomposition products a graded rotating resonant field should be created between RFQ rods. The amplitude of this $U_{rot}$ field should be not uniform along RFQ because the gas density along the axis of the RFZ is not uniform. The variation of the amplitude of this rotating field along the RFQ axis may be found empirically and may be close to that shown in the plot (47). This type of rotating field distribution is essential also for isolating of desired ions from the trapped ones shown in FIG. 1. To remove ions from the region close to the center of the flow a strong enough field is necessary. After coming to the regions with less gas flow and density the ions would be shifted to the front end of the RFQ by a decreasing electric field (48) and here less rotating field is required for stable ion rotation. Linearly decreasing the DC field (48) is preferred as it creates a linear increasing orthogonal field directed from the axis of RFQ (this is a consequence of the Laplace equation for electric field potential). The resonant frequency for rotation of ions with chosen m/z would be constant along RFQ in this case as the influence of such field would be equivalent only to some decrease of RFQ effective potential and not change its relative distribution. Ions with a given m/z value but with different collision cross section (45) and (46) may ultimately rotate at different places along the axis inside the RFQ. Thus in favorable cases it may be possible to distinguish between such product ions and even to decompose them further and separately. By gradually removing DC potentials differences between the left side and the middle of the RFQ as well as the rotational RF until these potentials are set to zero then the ions with larger collision cross section would be released first, return to the gas flow and would be recorded by the TOFMS. If it is desired to choose some of these remaining product ions for further transformation then retarding DC potentials forming fields (14) and (41) should be restored just before the remaining desired ions begin to enter the gas flow. If there is no desire to work with the remaining rotating ions in this cycle of measurements they may be removed by increasing the amplitude of the rotating field to move these ions to the rods to avoid confusion with product ions of newly trapped primary ions.

Figure 4:
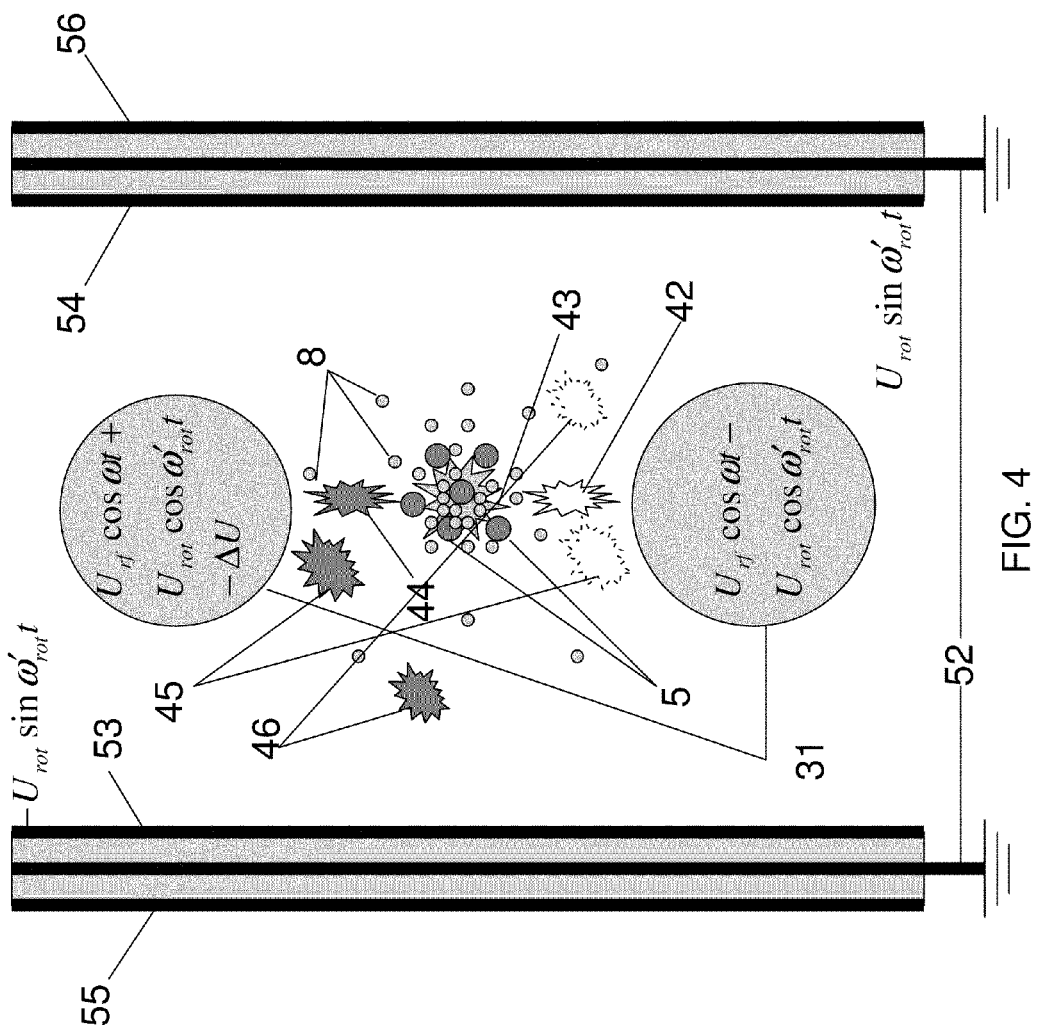
FIG. 4. Cross-section of one the sections of the RF multipole ion guide for one beam of a multibeam IM TOFMS showing the applied RF focusing and rotating fields for isolating of desired product ions from the first decomposition of isolated parent ions.

FIG. 4 shows a cross section view of one unit of an RF multipole ion guide taken from an array of ion guides used in a Multibeam IM TOFMS (described in co-pending patent application U.S. Ser. No. 11/441,766 filed May 26, 2006 and incorporated by reference herein) where cylindrical rods (31) and (37) are separated by grounded plates (52). To create DC and rotating fields independently for each ion beam, sectioned electrode plates (55), (53), (54) and (55) isolated from ground (52) are alternated intersperse with the pairs of cylindrical rods (31,37). Also illustrated in FIG. 4 is the beginning of the isolation process just after imposing a resonant rotating field onto some of the trapped product ions (45) and (46) (shown also in the previous FIG. 3) after the first fragmentation of the isolated parent ions (43) trapped in the region of high gas density and exposed to the collisions with admixture Ar (5). Product ions (45), (46), (44), and (42) are shifted by a DC and rotating fields from the region of heating where the parent ion (43) is shown. After releasing the product ions into the oTOFMS (where their m/z will be measured) by switching out the retarding potential and the rotating field, a new batch of isolated parent ions could be trapped and made ready for further investigations. Alternatively desired fragment ions could be trapped and fragmented allowing $MS^2$ measurement to also be performed in this case. Repetition of this procedure n times would give the possibility of implementation of $MS^n$ methods. This sequence of repeated trapping, fragmentation, and release and measurement of product ions and repetition of this sequence is applicable to any of the RFM embodiments taught in this application.

Figure 5:
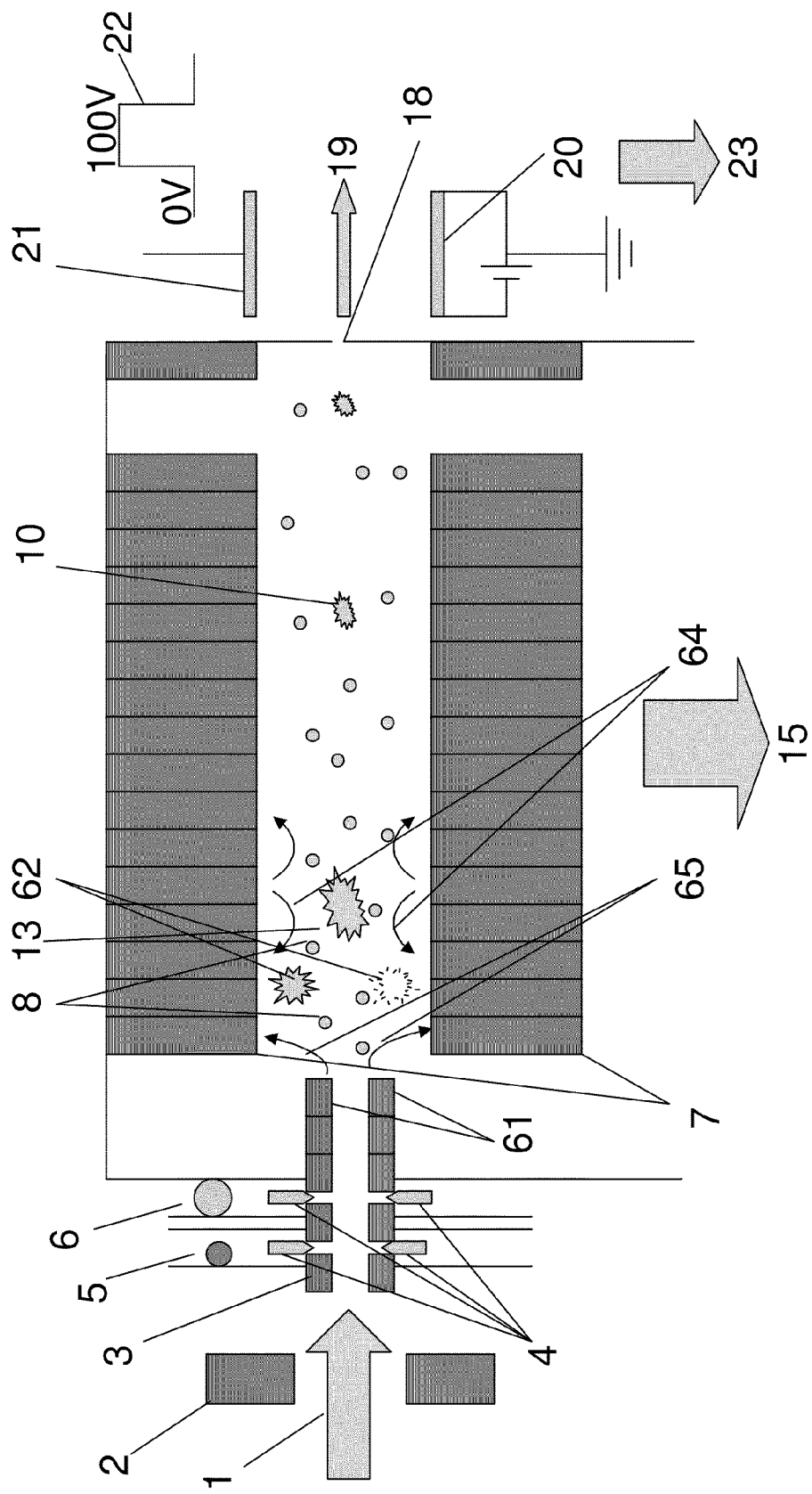
FIG. 5. Illustration of trapping of desired ions with chosen m/z value from multiple mobility separations by use of rotating and DC fields.

FIG. 5 illustrates an alternative way of trapping and isolating the desired ions by using resonant rotating fields and DC fields to selectively extract the a desired ion from multiple mobility separations of ions. In the most universal form of IM spectrometry a source of ions is pulsed and the pulsed ions drift through the mobility cell and separate according to their densities (which is reflected in their differing mobility drift times through the IM cell). In one example of this, a laser is used to pulse a MALDI ion source whose ion output is directed into a IM cell. At some time after the initiating laser pulse, the mobility resolved ions begin to elute as a function of time after the initiating laser pulse. Application of a rotating field on the first few electrodes next to the first electrode (30) of the RFQ (300) while intermittently applying a DC extraction between electrodes (61) and (30) will draw any ion which are eluting from the exit capillary (3). Thus by timing the application of this DC field relative to the initiating MALDI laser pulse, it is possible select ions with only a desired IM drift velocity. For removing only these ions from the dense on axis gas stream ion rotation is started ions at the beginning of the RFQ a field (65) is created between the final section (61) of the capillary tube and the first section of the RFQ (30). This field should be fairly weak so as not to totally overcome the focusing effect of the RF-field and not to move ions to RFQ rods. In this case ion rotation is initiated in the region close to the end of the exit capillary (3) where the residual gas density is lowest and which should result in a significant increase of mass resolving power with resonant ion rotation. For residual helium pressure of about 1 mTorr this resolving power may be 4000 or more. Highly efficient dynamic trapping of ions, which simultaneously have a desired m/z value and some interval of mobility drift velocity, can be achieved by selecting a resonant rotating field with it frequency chosen for selecting an m/z value and its amplitude chosen for a specific mobility cross-section which are then applied in conjunction with a small retarding electric field (64) (created over some distance from the beginning of the RFQ). The extraction field (65) is relaxed to zero and the weak fields (64) are manipulated to shift the trapped desired ions slightly downstream into a stable trapping region where they are purified over time by the rotating RF field. Repetition of this sequence of applying the timed extraction field (65) after the laser shot to move the desired ions out of the dense gas stream, manipulating the desired ions (62) by using the weak field (64) to shift the desired ions downstream into a trapping region, followed by relaxing the extraction field (65) to zero voltage to allow the next packet of desired ions to exit the capillary exit (3) allows filling of the trap with new (target) ions after each and every MALDI laser pulse. These new ions can be extracted and added to the already stored ions which can then all be and processed and stored for many seconds after the MALDI experiment is concluded. The mobility cross-section interval which can be trapped in a rotational orbit following this proceedure depends on the "radius" of the dense gas stream and the internal radius of the RFQ. For a realistic example, the "radius" of the gas stream is assumed 0.5 mm near the exit (61) of the segmented exit capillary (3), and the average radius of rotation of the desired ion is 1 mm inside the RFQ whose internal radius is 2 mm. A rough approximation of the range of IM cross-sections which can be initially captured into the rotating filed trap at this location is that ions with one half the mobility cross-section will expand into an orbit which hits the rods and are lost and the ions with twice the mobility cross-section will have an orbit which is too small to leave the dense gas flow along the RFM axis. The retarding field (64) should th be chosen small enough not to prevent any ions to move inside the gas stream but strong enough to retain rotating ions outside the main stream of the gas flow. The field (65) at the beginning of RFQ would prevent rotating ions from escaping from the end of the RFQ nearest the exit capillary (61) or alternatively fields (64) can be manipulated to move the rotating ions downstream where a trapping and storage region can be established. All of the other ions which have not been removed from the gas flow will consequently pass unimpeded under the rotating trapped ions and through the exit aperture (18) and enter After finishing the measurements of the ion MALDI-IM-oTOFMS spectra the laser ablation is terminated and the mass spectrometer is then used to process the unknown trapped ions which have been selected and purified according to their desired m/z and mobility within the rotating trap region Trapped ions having the desired m/z may comprise several different types of ions having the same m/z and different mobility values. It possible to process this collection of trapped ions at this time while no other ions are entering the buffer gas flow into the oTOFMS by using a programmed reduction of the rotating field amplitude to successively release ions back into the gas flow according to their decreasing mobility cross section. We first gradually decrease the rotating field amplitude to a value at which we begin to record ions in the mass spectrometer and at that point the rotating field amplitude is held constant until we no longer see ions or alternatively as soon as we observe the first ions we not only stop decreasing the rotating field amplitude but we also reinstate the retarding potential so that ions which are at this point re-entering the gas stream are stopped in trapping region of the main stream gas flow. After some delay time, which should be found experimentally. all the procedures for heating, transformation of ions and recording of mass spectrum of the products are performed. After that the gradual decreasing of the rotation field resumes to release the ions with higher mobility cross-section from their stable orbits and back into the gas stream is resumed so that ions may re-enter the gas stream and be transmitted directly to the mass spectrometer (zero retarding field) or further trapped and fragmented (maintaining RF rotating field amplitude constant and re-instating retarding field). When the next ion with chosen m/z and is recorded all the procedures described above are repeated once more. When the rotating field is zero the measurements are stopped at which point one has obtained the entire MALDI-IM-oTOFMS spectrum along with MS" of the trapped ions all in one set of timing sequences followed by a timing period of releasing all the trapped ions according to their collision cross-sections as well as any desired MS/MS spectra of the product ions. The procedures described around FIG. 5 may result in a reduction of time to perform the entire IM-MS" experiment since slow operations with gas flows may be repeated fewer number of times while still allowing the IM-MS measurements to proceed while desired ions are being accumulated. Manipulations on the trapped ions such as dissociation or reaction with neutral molecular adducts can then proceeds after the MALDI-IM-oTOFMS spectrum is completed acquired.

Figure 6:
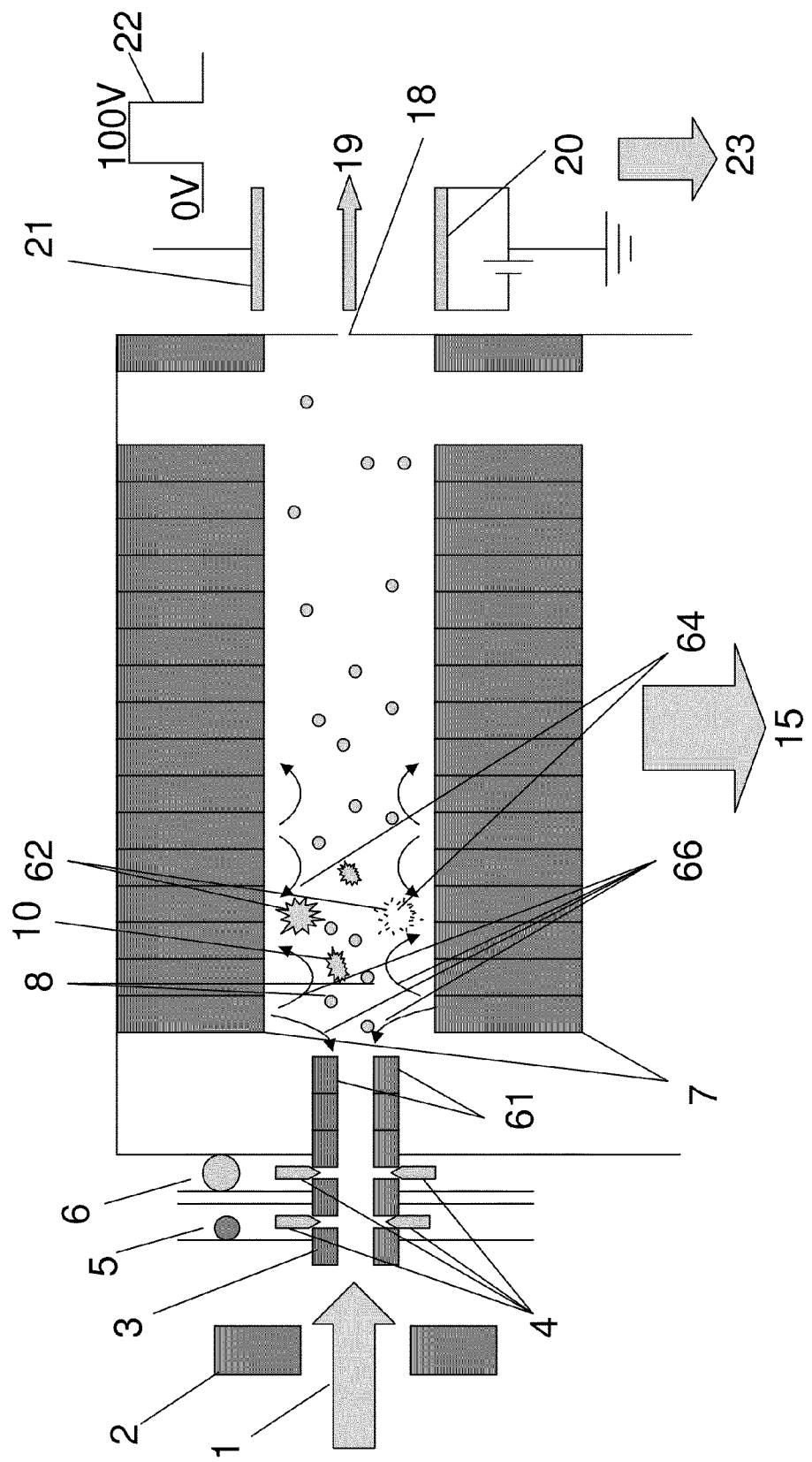
FIG. 6. Illustration of trapping of desired ions with chosen m/z value and mobility interval from multiple mobility separations by use of rotating and DC fields.

Measurement of Mobility Cross-Section by Slow Release of Rotationally Trapped Ions Back into the Gas Stream FIG. 6 shows some modification to the previous approach with the additional possibility to increase the resolution of cross-section measurement of the trapped ions using the RFM and rotational field trapping. In order to avoid trapping ions with mobility coefficients different from the desired some retarding potential (66) is applied to the first sections of RFQ rods all during the IM-oTOFMS acquisition time period for recording the untrapped ions except during the brief time (few tens of microseconds) time when the ions with the desired mobility cross-section are coming out of the exit tube (61). This potential (66) should be enough to prevent ions from moving outside the main stream of the gas flow but not so strong as to stop ion motion inside the main stream. At the moment when the desired ions just begin to pass the first sections of RFQ (7) the potentials on the first rods of RFQ are switched to form the accelerating field (65) shown in FIG. 5. Thus the ions of desired mobility cross-section begin to be trapped by the resonant rotating field. After the last desired ions pass the starting plane of RFQ (7) the potentials on RFQ sections are switched back to form the retarding fields (65) shown in FIG. 6.

Figure 7:
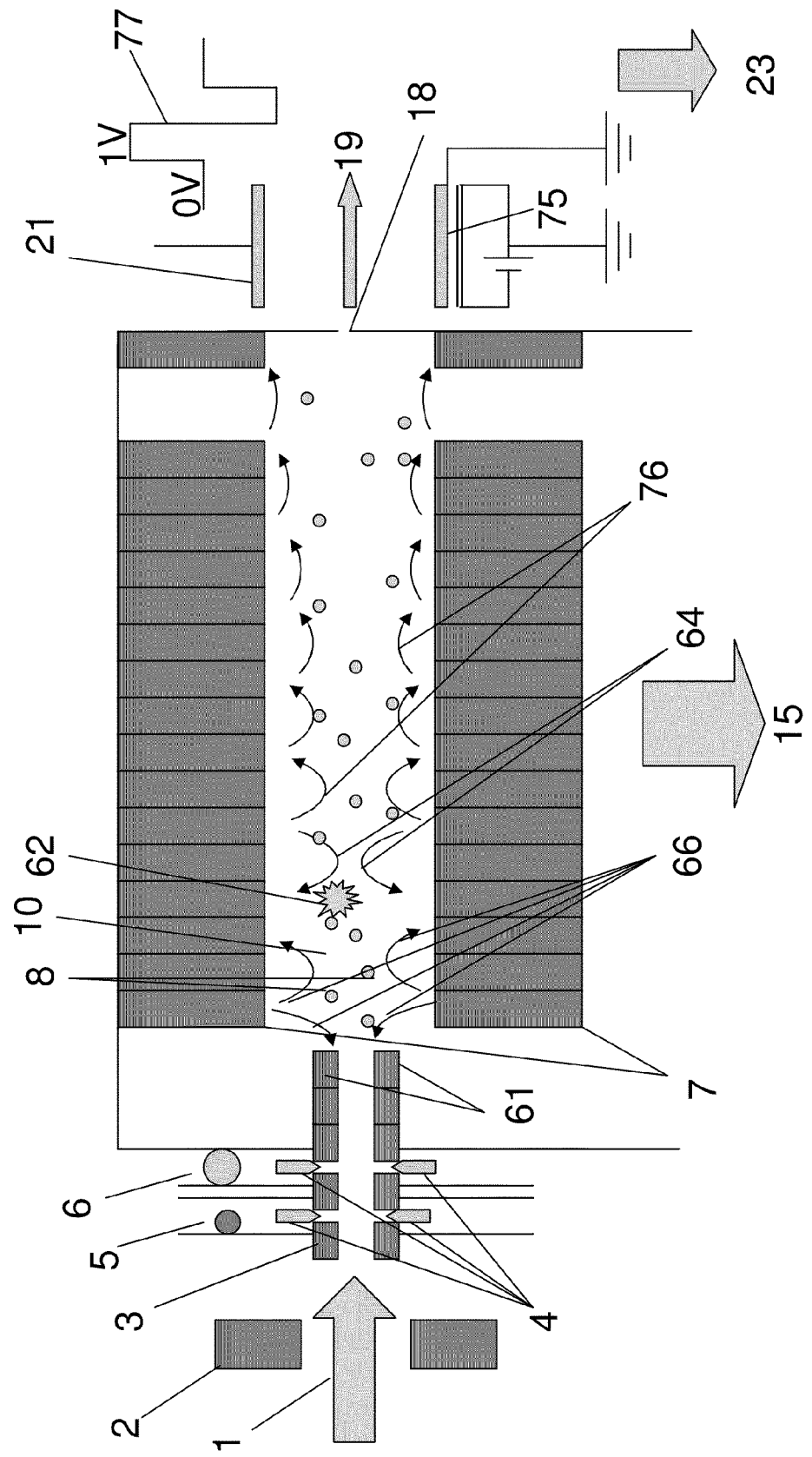
FIG. 7. One possible way of measuring of ion mobility crossection of ions isolated at low temperature conditions as shown in FIGS. 5 and 6. Also shown is an electron impact ionizer which can be switched to provide low energy electron capture dissociation of large multicharged positive ions.

After isolation of the ions by the method shown in FIG. 6 and in FIG. 5, In addition to recording the products of ion transformations, it is possible also to get some information about collision cross sections of these ions over a wide under wide temperature range. This information is difficult by standard mobility measurements. FIG. 7 illustrates one possible way to obtain such estimations over the temperatures below room temperature down to the region close to absolute zero by forming a decreasing electric field (76) in the direction of the gas flow along RFQ and no admixtures to He atoms (8) flow are added. For measuring at temperatures higher than room temperature some admixture of Ar (5) atoms may be inserted into the He flow. The field decrease should correspond to the decreasing of the gas density along the flow so as to provide constant drift velocity of ions above the velocity of the gas flow. In conditions of low or moderate pressure mobility measurements this gas flow may be considered as a molecular beam coming from the exit tube (61) with the axial velocity close to the mean squared gas velocity for the room temperature and some divergence corresponding to the temperature of the gas. How to measure this axial velocity and the average angle of the gas divergence is explained below. Switching out the rotating field makes previously trapped and rotating ions (62) to re-enter the gas flow as the increased in the retarding field (64) also prevents them to move along the flow and RF focusing field would push them to the axis. After some time sufficient to collect all ions near the axis the polarity of retarding field (64) is changed and its strength is adjusted to form at that place a slowly decreasing axial electric field. Under the influence of the gas flow and the axial electric field ions after some time would achieve the velocity above the velocity of the gas flow. The value of this additional velocity for a given field strength gives the mobility of the ions from which their collision cross section may be estimated for known gas density. The temperature of the ions would be proportional to the square of this additional velocity and may be estimated from measurement to be described in the following sections.

The value of the total ion velocity as well as the time of their motion after switching the polarity of the retarding field (64) may be estimated via multichannel TOFMS data as also described below. The velocity of the gas flow and its density is measured by electron impact ionization (20)-(21) of the carrier gas and any admixture atoms in the mode shown in previous figures. This ionization is initiated by applying an anode voltage pulse (77) (it is also possible to implement electron capture dissociation technique for large multi-charged ions in the case where the voltage pulse width is chosen just to "stop" electrons in the region of the flow (19) coming out of the exit orifice (18)). A cathode with indirect heating (75) gives a reduced energy spread of the electrons and is desirable for use in this application. Sophisticated and effective designs of a low energy electron ionizer are known in the art and may be found in the literature. This electron impact and electron capture source enables estimation of the collision cross section for the RFQ isolated ions in FIG. 7 for the same temperature by creating the small decreasing retarding electric field of the same strength which provides the same steady state absolute value of velocity difference between ions and the gas flow. The comparison of the results of two such measurements will give the dynamics of the cross-section variation as a function of ion temperature by measuring the change in the relative velocity of ions and buffer gas atoms. Also it would provide a way to estimate small changing of the ion velocity due to collisions with gas after exit orifice (18). This effect is slightly different for both cases since because the accelerated ions would move faster after exit (18) they would then have fewer collisions in this region compared to the collisions of the retarded ions. Such an approach combined with controlling the dense gas temperature by injecting the necessary heavy admixture gas into the dense gas flow may also be used for investigation of the formation and desolvation of cluster ions under low temperature conditions. Comparison of cluster ion distributions measured for the same accelerating and retarding fields would enable estimation of "equilibrium" conditions for cluster formation.

Figure 8:
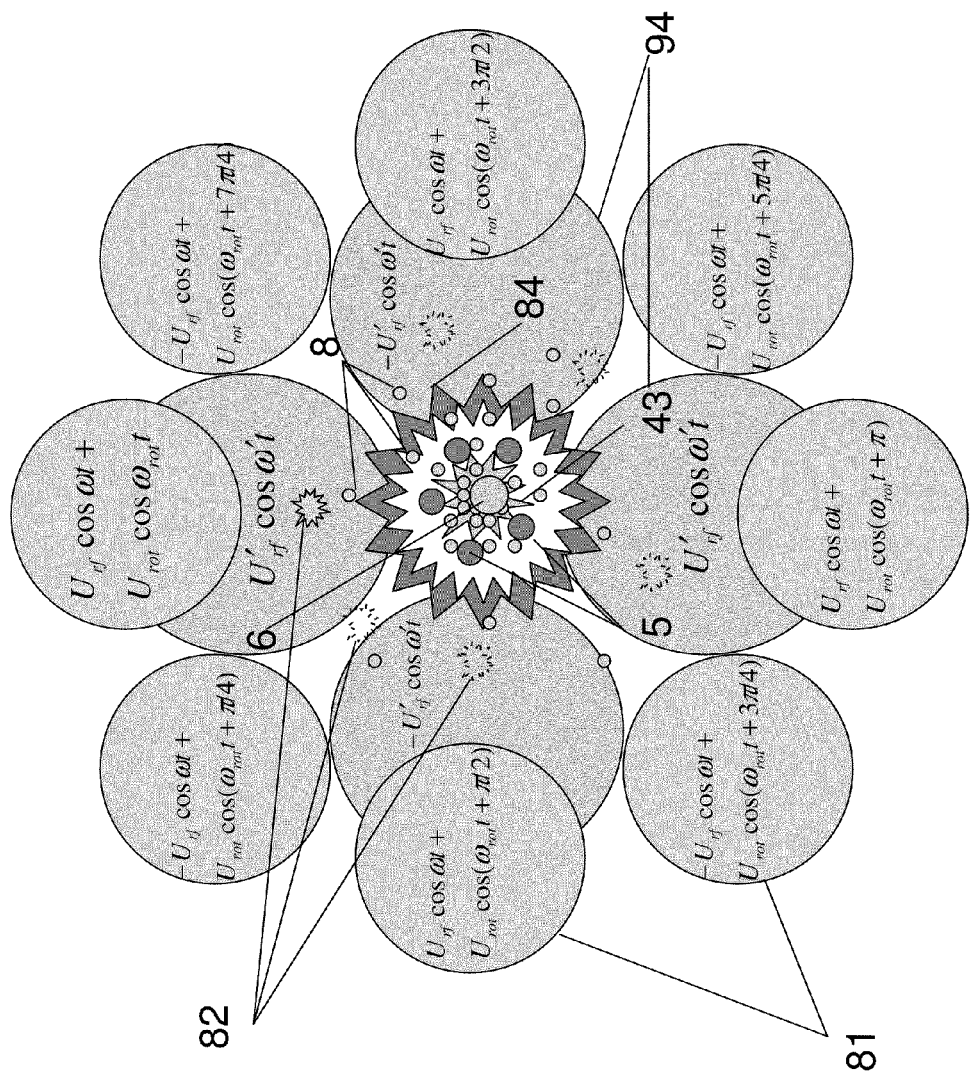
FIG. 8. Cross section view of combined ion guide with RF-octapole for the trapping and isolating of ions and RF-quadrupole for focusing ions and controlling their transformations under low temperature conditions.
Figure 9:
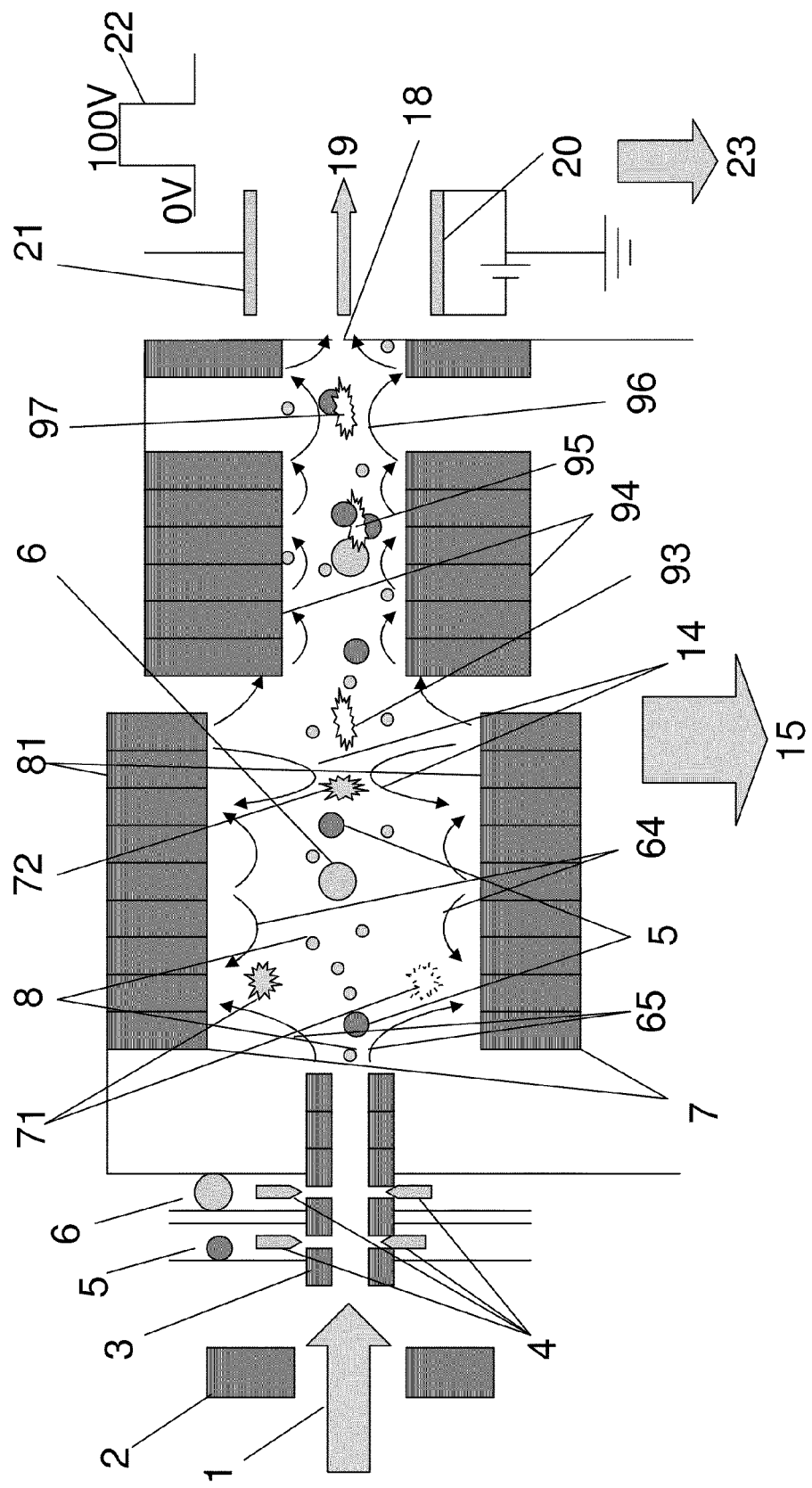
FIG. 9. Illustrates the view along of the combined ion guide of FIG. 8.

The methods described above may be implemented not only in a single RFQ ion guide. It may be even more effective in some cases to use a combined ion guide such as, for example, those shown in FIG. 8 and in FIG. 9 Using an RF-octapole (or multipole with number of poles more than 4) at the beginning of ion guide for trapping, isolating and transformation of ions may be more preferable at least in some embodiments of the present invention. A faster production of an effective focusing potential for octapole (ideally it is described by the polynomial of the fourth order in contrast to second order polynomial for RFQ) would result in more narrow distribution of rotating ions (82) and less probability of their discharge on octapole rods (81). Somewhat better separation of ions with larger m/z is expected for RF-octapole. For creating rotational fields the phase shifts between adjacent rods (81) of the octapole is $\pi/4$ instead of $\pi/2$ used with the quadrupole. Product ions may easily produce corona like paths (84) under the influence of DC-fields directed to rods (81) since the effective focusing potential is reduced as a polynomial of the fourth of distance from the rods to the axis instead of the second order of this distance in the case of the RFQ. Thus these product ions may faster come away from the region of heating by Ar atoms (5) and decomposition by collisions with Xe atoms (6) thus providing even cleaner conditions for ion decomposition than when using the quadrupole. The final part of the ion guide may then be a quadrupole as it provides better focusing and cooling of the ions. Its rods (94) built of isolated sections allow to also create an electric DC field inside to provide the previously mentioned functions of a low temperature reactor for primary ions and their products. As an example in FIG. 9, such product ions (93) may be an ion with less charge to cross section ratio than that for the primary isolated ions (73). This product ion (93) can overcome the retarding electric field (14) and form some cluster ion (95) (either intrinsically or with intentionally added admixture gas) while moving inside the cooled gas flow. Under the influence of a de-clusterization field (96) this cluster ion may be decomposed partly (97) and kinetics of this decomposition may be investigated by changing of this field (96) and recording the resulting cluster ion distributions in the mass spectrometer.

Figure 10:
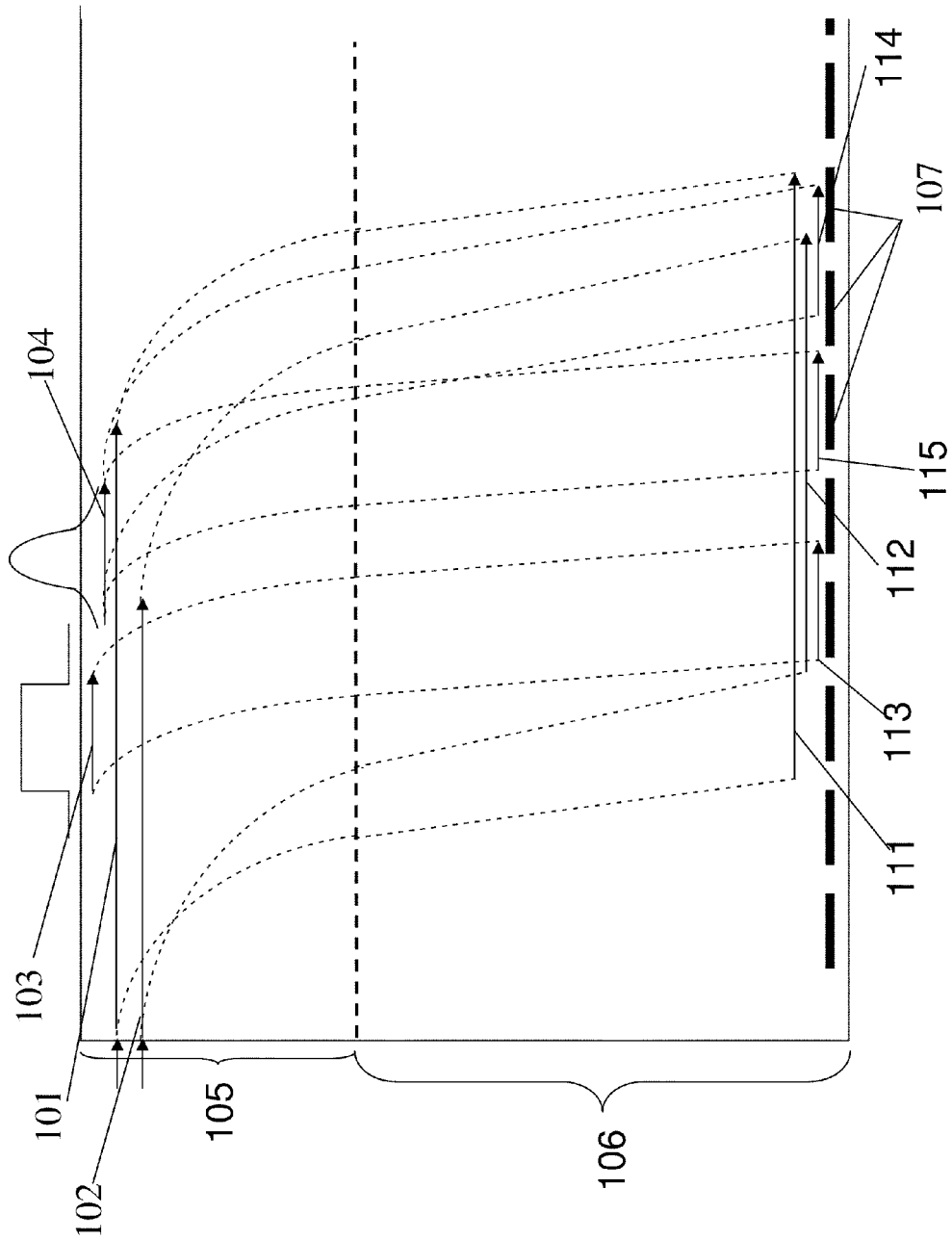
FIG. 10. Schematic view of linear TOFMS with multichannel data recording showing the possibility of measuring of ion drift velocities and divergence of the ion beams and distinguishing the ions formed by electron impact inside the gas flow after exiting the RFQ ion guide from the product ions released from within the RFQ after switching off the retarding trapping potential.

An important capability which is added to the oTOFMS allowing such kinetic investigations is multichannel data recording and position sensitive detection. The TOFMS may be reflectron type (see., e.g., U.S. Pat. No. 6,683,299 and U.S. Pat. No. 7,019,173, and published U.S. Patent Application 2005/0127289 A1, all of which are incorporated by reference as though fully set out herein) which is more suitable in our case or even a linear TOFMS. A schematic of a linear oTOFMS suitable for the considered measurements is shown in FIG. 10. It is similar to that described in U.S. patent application Ser. No. 11/441,766 filed May 26, 2006. Here for simplicity a single beam instrument is considered. The important property of this instrument is the sequence of anodes (107) which is not shown finished in the figure. These anodes are connected periodically with corresponding channels of the TDC. For example for an eight channel TDC the first 8 anodes are connected sequentially to 8 channels of TDC. The 9th anode is then connected in common to the 1st anode into the 1st channel of TDC, the 10th anode in common with the 2nd anode goes into the 2nd TDC channel and so on. The length of ion package inserted into TOFMS is controlled to be less than the length defined by the first eight anodes so no confusion of ion signals will occur. Alternatively, more TDC recording channels may be added so that each anode is independently measured into its own recording channel. Furthermore, each anode may have its own TDC channel each channel of which is capable both of measuring the arrival time and the analog intensity of the portion of the electron pulse from the MCP which lands on one anode. When one ion strikes the ion detector, the resulting electron cloud may be spread over multiple anodes so that, after charge centroiding, the position and time of arrival of the ion at the detector plane can be measured with high time and positional accuracy. Such position sensitive detectors are known in the art and their use allows even more accuracy when making the angular and velocity measurements described in the following sections. The velocity and angular distribution variations may be interrogated by electron ionization of the gas components (103) or after switching out the retarding potential (14) for releasing of the product ions after their transformations (104). Also it may be controlled by the timing the ion insertion into the acceleration region. Ions with larger velocity (101) would fill a longer path than that of slower ions (102) during the insertion time of ions into the field free acceleration region (105). The region (106) ideally is field-free all the time even during the application of an orthogonal extraction pulse to accelerate ions through section 105 and onto the detector. Thus fast ions would be recorded over a wider spatial range (111) on the multianode detector (107) than slow ions (112). If these ions are uniformly distributed in time of arrival the numbers hitting the first and the last anodes and relative intensities recorded at these boundary anodes in comparison with internal ones may give a good estimation for velocity of ions. For non-uniform distribution of ions along their path, which is usual the case for ion mobility separated ions, it is possible to shift the ion package as a whole along the insertion path of the orthogonal extraction region (105) by delaying the start time of TOF acceleration relative to when the constant duration of insertion is begun. The shift of location of data in recording line (107) would give the velocity of ions as a function of this time shift. Normally (when no DC fields are created in the final part of ion guide) the velocity of ions should be close to that of the gas flow. When accelerating or retarding fields like (76)—FIG. 7 or (24)—FIG. 1 are applied to the ion the measured velocity is directly connected with the temperature of cluster ions (it is proportional to the square of this velocity difference) which thus provides an opportunity to estimate kinetic parameters for the decomposition of cluster ions. This possibility is more directly applicable when ion transformations are performed on ions trapped in the middle of the ion guide. In the frames of the simple model of independent attachment of atoms or molecules to some sites on the ion it is possible to decompose the observed intensity distributions of cluster ions into the sets of probabilities of attachment to these sites. Such procedure may be performed also for other processes like H/D exchange or protonation and deprotonation of multicharged ions. For the problems for deconvolution of the distributions of multicharged ions and for H/D exchange mass spectra processing, this possibility was previously demonstrated in the art (see, M. O. Raznikova, V. V. Raznikov: "Protonation Probability Estimation of Amino-Acids in Peptides and Proteins by their Electrospray Mass Spectra" *Chimicheskaya fizika*, v. 20, N4, c. 13-17, 2001 (in Russian); M. O. Raznikova, V. V. Raznikov: "Determination of the extent of activity of H-atoms in ions of polyfunctional compounds by H/D exchange mass spectra" *Chimicheskaya fizika*, v. 24, Ni, c. 3, 2005 (in Russian)). Plotting the probabilities of attachment on a logarithmic scale as a function of inverse temperature will give estimations for the energy of atom or molecule attachment (as well as activation energy of H/D exchange or proton affinity) for each site in the ion and the frequency factor. Independent and quasi simultaneous measurements of gas flow velocity are provided by recording of gaseous ions (103) produced by electron impact ionization (20)-(21), having a rectangular peak shape due to the shape electron pulse (22). Location of the electron impact produces ions (103) on the detector area (113) depends on this velocity, length of ion path, time shift between electron pulse and extraction of ions in TOFMS, m/z value of ions, and the TOF acceleration voltage. Among these ions (103) all neutral admixtures to the gas flow may be recorded including neutral products of decomposition of isolated ions. The latter may also be produced mainly by charge exchange between $He^+$ ions and neutrals which have much less ionization potential. Such ions may be valuable for providing reliable structure information. For recording of negative multicharged ions an attachment of $He^+$ ions may result in dissociation of these ions similar to electron attachment dissociation of multicharged positive ions. Ions coming after switching of retarding potential (14) (FIG. 9) should produce a narrow bell-shaped (close to Gaussian) peak whose location (114) on the recording plane is connected with collision cross section of ions and their mass and charge. Thus overlapping ion peaks would be resolved by measurements of ion collision cross sections illustrated in FIG. 7 Electron attachment dissociation (or laser dissociaton) of these ions may be additionally valuable in this case as it would give a set of ions with different m/z values which would simultaneously give structural information while still allowing to estimate ion velocity by comparison of locations of these ions (114) (fragment) and (115) (parent) the in recording plane. The shift between them is equal to the product of this velocity and the difference in ion drift times in TOFMS. It is possible also in some cases to use multichannel position sensitive recording to estimate the divergence of ion beams which directly gives the translational temperature provided that the corresponding axial velocity was measured before. For this it is necessary for the divergence of the mobility buffer gas beam to be more than the width of anodes (107). Alternately shifting mass or mobility resolved ion packets from successive insertions into the oTOFMS region (105) between the first anodes and the last anodes by appropriate delay of acceleration start relative to the start of ion insertion would give information about divergence of the ions. This shifting technique of course becomes unnecessary if each anode is connected to its own analog and timing measurement channel in a fast position sensitive detector. This measurement is simpler for light ions such as of He, Ar, Xe, but it is possible to do for large ions too particularly when a PSD of high spatial resolution is employed. This is important in the case where the large ions are heated due to some fields at the end of RFQ so their divergence would increase proportionally to the square root of the temperature of heating.

Figure 11:
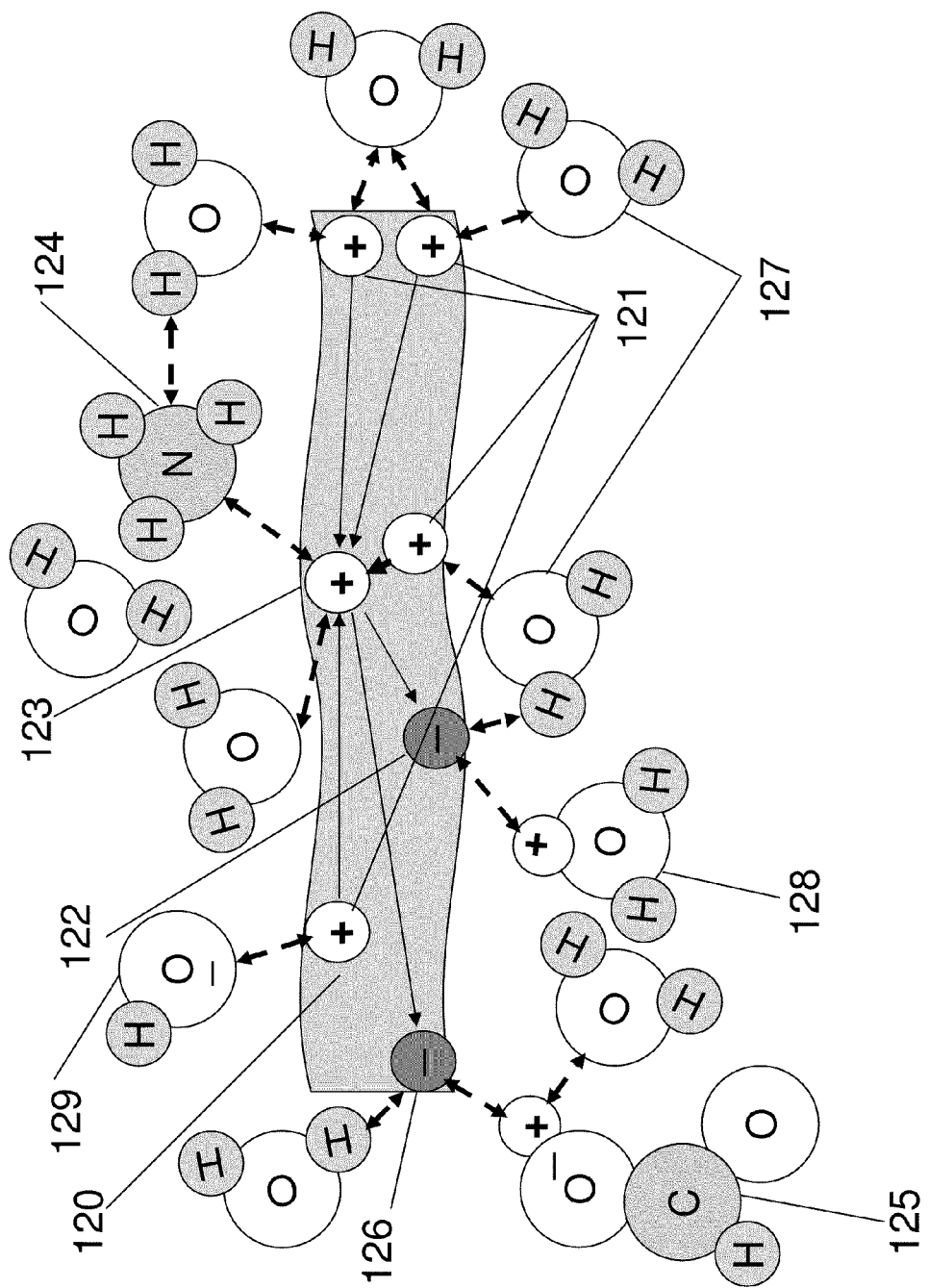
FIG. 11. Schematic view of possible processes of proton exchange for different sites of a biomolecule.

The new method of ion heating herein described by using heavy admixture atom impaction in the gas flow has the same advantage of direct heating of the gas compared to heating of ions via moving them by electric field. It is expected in the present case that ion temperatures would be fairly uniform for all trapped ions independent of their structure and charge. Thus it may be possible to use the process of charge exchange for multicharged ions (peptide and protein, for example) to provide information about proton affinities, averaged local electric field inside the ion, and for formation of clusters. FIG. 11 illustrates the idea. Schematically shown multicharged ion (120), (peptides for example), have several possible locations for positive charges (addition of protons for basic residues) and negative charges (removal of protons from acidic residues). If an admixture molecule with large proton affinity (ammonia molecule 124 is shown as an example) comes close to some proton location (123) and this molecule has a chance to capture the proton, then the effective charge of the ion is reduced from 3 to 2. On the other hand, an admixture molecule with a weakly bounded proton (formic acid is shown— 125) can attack a negatively charged site (126) where it increases the peptide ion charge from 3 to 4. After these proton transfer reactions, formation of positively charged $NH_4^+$ ion and negatively charged $HCO_2^-$ on are possible. To easily remove these product ions from the multicharged ion it is possible to use an excess admixture of polar molecules in the gas flow (like water (127), for example) to cluster with the ion. Thus the small ions would be associated with water molecules and may be removed from this large cluster ion more easily. The other possibilities for removing ionized small admixture ions from the peptide charge transfer site is to transfer the admixture ion protons to water molecules to form $H_3O^+$ ions (128) or to draw protons from water molecules to produce $OH^-$ ions (129). These water ions themselves may provide charge exchange processes with the bio-ion as shown in FIG. 11 as illustrated with the use of two-headed arrows. The probabilities of such events are dependent both on ion temperature and on the difference between proton affinities of the attacking molecule (or ion) and the corresponding ion site. Separation of the charged species to "infinity" in principle give the proton affinity of the ion site (123, for example) but in fact should also include a contribution of local electric field potential created by other positive charges of the ion (121) and the negative ones (122) and (126), shown by arrows. The proton affinity of the corresponding residue in the ion without influence of a local electric field may be estimated by measuring before proton affinities for corresponding small single charged ions. For a large enough solvent water cluster shell around the bio-ion and relatively small concentration of admixtures of basic and acidic molecules in the gas flow the charge exchange processes with the bio-ion should be provided mainly by water ions (as occurs in-vivo aqueous solutions wherein the main factor controlling this charge exchange process is the pH-value). To estimate the pH-value in our case it is sufficient to record the corresponding cluster ions and calculate their average composition. It is possible to switching out the cluster which have formed in the gas flow so that the composition of the clusters would also be "frozen" so as to conserve the steady state equilibrium distribution. To accomplish this, it is necessary to take into account that molecules of water, ammonia and formic acid have significantly more energy than helium atoms and corresponding energy of thermal oscillation of the ion so their impact on the biomolecule in steady state conditions would provoke on average some evaporation of the corresponding molecule. Spontaneous evaporation (exponentially dependent on ion temperature) can also take place but it should be significantly less. Thus if we reduce proportionally the concentrations of the considered admixtures and conserve the temperature of the ion (by a corresponding increasing of Ar admixture) up to the moment when these admixtures disappear totally and after that to quickly switch out the Ar flow, then the steady state composition of ion clusters should be conserved with good precision. Probabilities of charge retention by different sites of the ion can be calculated via intensity distributions of multicharged ions by the method already mentioned (M. O. Raznikova, V. V. Raznikov: "Protonation probability estimation of amino-acids in peptides and proteins by their electrospray mass spectra" *Chimicheskaya fizika*, v. 20, N4, c. 13-17, 2001 (in Russian)). For small temperature intervals, logarithmic plots of the multicharged ion intensities as a function of the inverse ion temperature would allow calculatoinal estimates of the proton affinities of the corresponding sites. Another possibility is to use these estimations of proton affinities for predicting conditions for creating a desired value of the average ion charge. This may be important to perform additional separation of isolated ions similar to the isoelectric separation of biopolymers in liquid and gel solutions. For high enough ion temperatures the transitions between different ion charge states as well as between different compositions of the clusters under the given flow of water, basic and acidic molecules would be fast enough. Thus it is possible to consider that bio-ions slowly moving in the gas flow and under electric fields in the RFQ isolation region have a constant charge and cross section which is equal to its average charge and cross section of clusters. This is the same assumption forming the basis of isoelectric biopolymer separation in liquids and gels which results in significant resolving power of this method compared to the case when ions with fixed charges are moving. This is true in our case too. For example, a 10% difference in average charge may be less than one charge for small charged ions but it provides a 10% difference in mobility of ions which are large and these ions may be easily separated by applying in the gas flow an appropriate retarding potential which can stop more highly charged ions but release ions with less average charge. It may be expected that resolving power of this separation would increase with decreasing of the average ion charge. Simulations show that large enough ions in a physically reasonable RFQ can be separated if they have mobility difference of about 1%. After isolation of some multicharged ions (or ions which are expected to have many sites to be charged) many manipulations can be performed with and on theses isolated ions. It may be useful, for example, to try to first determine the maximum possible charge number for the given ions. For determining maximum positive ions charge states a concentrated flow of acidic molecules combined with water molecules should be directed onto the ions while the temperature is regulated, perhaps, by some additional flow of Ar atoms. After that, all admixtures to the gas flow are removed, the retarding potential is switched out and ions are recorded. If necessary, the cluster shell may be removed by strong enough heating by Ar admixture flow. In cases where we observe ions with different numbers of charge it may mean that either steady state conditions are not achieved or that the isolated ions do not correspond to the same molecule. In case fragment ions are observed it means that for the temperature used such multicharged ions, unfortunately, are not stable. In this case complimentary ion pairs may be found: two ions with sum of masses being equal to the expected mass of the ion. In the event that some of these pairs possess different number of total charges than the isolated ions this may indicate also that a non-uniform or steady state conditions are not achieved. It is possible to try to estimate the number of sites in the ion where negative charges may be located. For example, for peptides and proteins usual sites for negative charges are acidic residues: glutamic acid, aspartic acid and also acidic group at the C-end of the molecule. These sites may be "closed" in a sample of control molecules by specific chemical reactoin via formation of esters by some admixture molecules added in the buffer gas flow such as methanol, for example. In this case ion composition would be changed by some substitutions of OH groups by $CH_3$ groups. In case several ions with different number of such substitutions are observed the isolated ions may be also non-uniform or steady state conditions are not achieved. Kinetics of these processes (in case some water admixture is added also to the gas flow for having reverse reaction-hydrolysis of ester bonds) may be investigated using the same approach, mentioned above for decomposition of intensity distributions of ions with different number of such substitutions. Probably, in this case some conclusions about the types of acidic sites in the ion and influence of the ion environments for these sites may be made. Determination of the number of positive and negative charges sites is essential information for information about proton affinities of different sites in the molecule as well as an averaged internal electric field in the ion. Additional separation of isolated ions may be performed, for example, in the following way. At first the retarding potential is adjusted to stop all these ions with average charge more than 1 and release singly charged ions or with less average charge. In case of measuring of multicharged positive ions the relative concentration of basic molecules (may be stronger than ammonia) in the flow is increased gradually up to the moment of recording the first two expected single or more charged ions. Two ions are necessary to record to estimate the time when all isolated ions may be released in case they have the same average charge. After that stronger retarding potential for stopping ions with average charge significantly less than 1 (0.1, for example) as shown in FIG. 3 (41) is switched on. Thus low charged ions would be accumulated in a new position and if some of isolated ions have enough extra average charge they would stay at old place. After some time sufficient for shifting of "all" isolated ions to a new position the rest of the ions (if any) which are located before the first retarding potential are removed by a corresponding rotating field to rods or they may be conserved for further measurements by gentle excitation with a sum of rotational fields resonant for each ion charge possible for isolated ions. So ions which have just been so selected may be investigated separately from their neighbors from the previous isolation. After releasing these ions or their products of transformation the remaining ions which are just rotating may be returned into the gas flow by switching out of rotation field and they may be subjected to further separation and all other procedures what was done with the first portion of selected ions.

Figure 12:
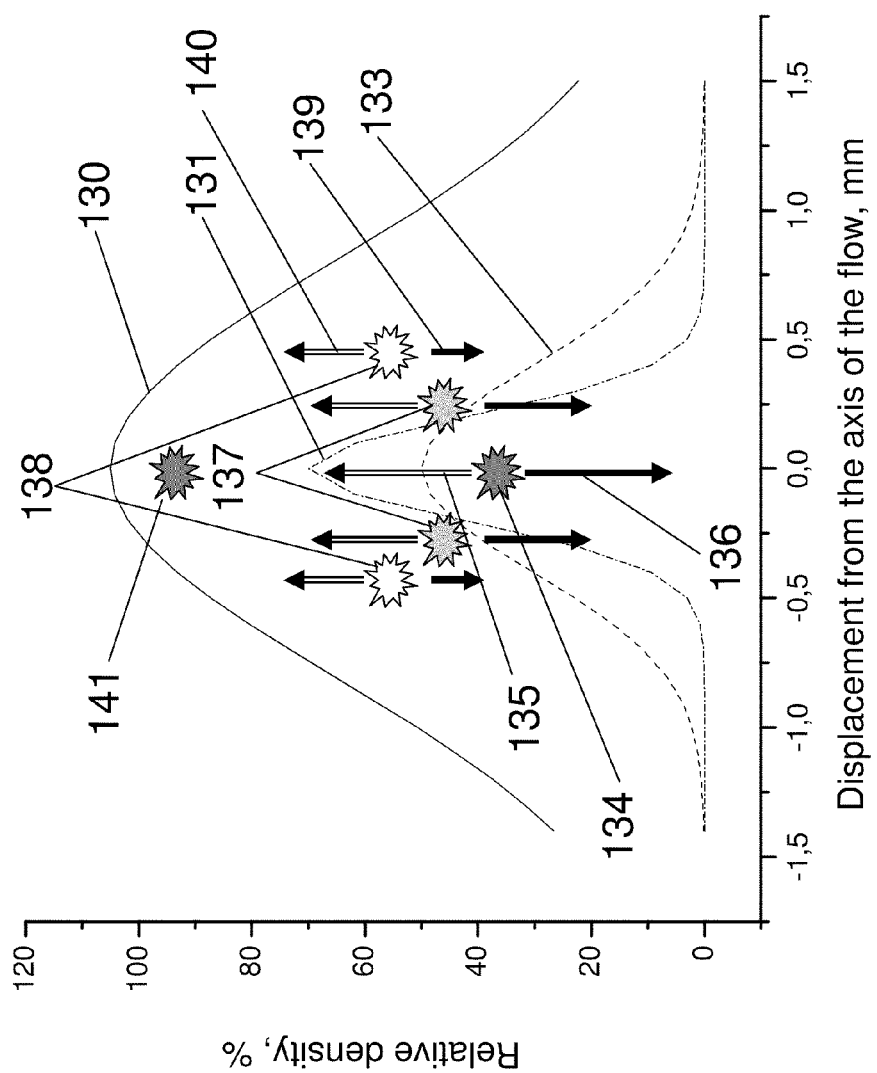
FIG. 12. Qualitative view of density distributions for different components of the gas flow at a cross section of the RFM at some distance along the RFM after the IM exit tube.

In some cases it is necessary to further select the ions. Non-uniformity of selected ions may be understood by recording of their mass spectra which reducing the retarding potential in conditions when flow admixtures remain constant. To maintain high enough temperature of the ions to prevent them from forming too large clusters a decreasing retarding electric field along RFQ would be created to provide close to constant drift velocity of the ions as it was described previously in the sections devoted to the measurements of cross-sections of the ions. The difference here is that ions during their drift in RFQ would be subjected to relatively fast steady state transitions between different charge states and compositions of the cluster shell. Thus the measured average velocity of such ions by multichannel data recording as described in the previous sections would correspond to some average ion formed in conditions slightly different from those for the region of isolation. The main difference in our case would be a somewhat more relative steady state concentration of acidic molecules as they have less angular divergence than other admixtures; thus their approach to steady state conditions in the gas flow would occur more slowly than for other admixtures. In case to conserve as far as possible the conditions of the cluster formations it would be possible to get an upper estimation of the average mobility of primary ions selected and subsequently released by reduced retarding field. At first ions having low charged and larger cross section ions would be released. Noticeably different average m/z values of the ions or significant difference of their average velocities for different releasing retarding fields would indicate that these ions are not uniform. Using rotating field excitation of the drifting ions may allow the removal of undesired ions from the flow and estimate the average m/z value of ions of the interest in the flow. It would give a low estimation of average m/z of these ions in the region of isolation and it may be used for additional separation of desired ions. The possibility of this separation is based on different distribution of different admixture molecules across the gas flow on some distance from the exit tube as it is shown qualitatively in FIG. 12. Molecules such as formic acid (131) which are heavier than ammonia would have about 1.64 times less divergence than that of ammonia molecules (133) which is about twice less than the divergence of He (130). The water molecules having molecular weight close to that of ammonia would have almost the same divergence. Thus at some distance from the flow axis the relative concentration of ammonia would rapidly increase in comparison to that of formic acid, therefore ions shifted from the axis (137) would have significantly less average charge than those near the axis of the flow. Ions would restore their previous average charge after returning onto the axis to the place (134) where the retarding electrical force (136) is compensated by the dragging force of the gas flow (136). The compensation may also be done by applying a sum of rotating fields to selected ions located in specific regions along the RFM. To select the desired ions the interval of rotating frequencies should correspond to the interval of m/z values starting at an m/z slightly below the estimated average m/z ratio of the desired ions which are in the flow and up to slightly beyond this ratio with z being equal, for example, to 0.1. The amplitudes of the rotating field are increase so that some ions would move off of the axis to a distance determined by their having an average charge of ~0.1 (138). Thus, the ions could overcome a strong retarding potential, (which can be produced in this case by relatively small retarding force (139) which is less than the dragging force (140) of the gas flow) and would therefore come out of the rotation region, return to the flow axis (141) and then increase their average charge. They can then be recorded or alternatively isolated for further investigations. The isolation of the ions is not very dependent on momentary increases of the rotating field amplitude or frequency occasional increase of their rotation radius beyond that defined by their average charge of 0.1 would result in commensurate reduction of the average ion charge which then causes the ions to moves from conditions of resonant rotation and reduces their rotating radius to the region where the average charge is 0.1. By measuring m/z values and the velocities of ions as they are being gradually released, the appropriate amplitude of the rotating field which is suitable for releasing the desired ions may be determined. Switching on the additional retarding potential at the moment the desired ions start to be detected in the mass spectrometer and stopping any further increase in the rotating field would allow isolation of the desired ions for further investigations.

The generation of rotating fields for a set of chosen frequencies and amplitudes may be important from another point of view as well. Mass spectrometry and IM/Mass Spectrometry. For example, such known problem of multicharged deconvolution of electrospray mass spectra may be a really difficult problem for investigation of heavy mixture of bio-ions. Usual mobility separation in this case may even complicate the problem. It may separate ions corresponding to the same biomolecule having the same number of charges but different cross sections due to different distribution of charges inside the ion. From that point of view, fast randomization of charge distribution inside the ion during the process of mobility separation may be important for real separation of different biomolecules. Thus, it may be advantageous to first trap ions from the initial gas flow not only ions for chosen m/z and mobility values but all ions with chosen mass with all possible charge numbers and within a range of expected mobility values for each possible charge number. Such trapping may be provided by switching on a predetermined sum of harmonic rotating fields with given set of frequencies and amplitudes in the way as shown in FIG. 5 during the ion flow. Furthermore, all these trapped ions are inserted into the gas flow by switching out the rotating field and are then accumulated at some position inside the flow by applying strong and short duratinon retarding potential. By the procedures just described ions may be separated, using controllable flows of water, basic and acidic molecules, on the basis of their different abilities to obtain and lose charges and form clusters in such flows. This separation would be a real separation of biomolecules and not a separation of different ionic forms of the same biomolecule as may occur in the usual practice of mass spectrometry and ion mobility separations. In the case of large biopolymers investigations where the biopolymer has multiple sites for both positive and negative charges it may be possible to use a simpler method of separation based on providing conditions close to the isoelectric point for the molecule of interest. The idea is to provide such conditions at the region close to the beginning of RFQ (154) in FIG. 13, where the gas flow is not yet diverged significantly and the relative densities of admixtures near the flow axis: (5)—Ar, (151)—formic acid, (152)—ammonia, and (153)—water are close to those at the beginning of the supersonic flow. Switching on two strong short retarding potentials: (159) to stop positive ions (154) and the next (160) to stop negative ones (155), would allow only species with average zero charge (156) to come through them. These particles moving with the gas flow would come to the region where due to different divergence of acidic and basic admixtures the relative density of acidic molecules is more than that in the region of retarding potentials and the considered particles would became gradually preferably positive (157). Maximum increase of this relative density in case of formic acid and ammonia is ~2.7. In case it is enough to provide average charge of the molecule of about 1 the corresponding ions (158) would be recorded with applicable efficiency. It is important that molecules which have an average zero charge do not come out of the gas flow before their charge is sufficiently increased. Negative charging of these molecules would result as they came to the edge of the gas flow since the relative density of ammonia is larger here than near the axis of the flow. Therefore these molecules with average negative charge would be returned to the gas flow by RF-focusing of the quadrupole.

Alternatively it is possible to provide conditions close to the isoelectric point of the molecules of interest in the region rather close to the end of RFQ where gas flow composition near the axis is close to a steady state situation. In this case the average charge of the ions which could pass through positive and negative potential barriers like (159) and (160) in FIG. 13 would be close to zero up to the exit (18) from RFQ. On the other hand the gas flow density is low enough in this region so that the average time between collisions of the ions with gas molecules is much less than that at the beginning of the RFQ. Thus the average frequency of ion transitions between different charge states (provoked by collisions) may be not so large and significantly less than the frequency of RF-field (few MHz usually). It means that ions with average zero charge but consisting at each moment of some mixture of positive, negative ions and zwitter-ions would be focused to the axis of RFQ as both positive and negative ions are influenced effectively by the same force directed to the axis and zwitter-ions could be transformed to usual (not zero charged) ions after some time (hopefully less than the time of these ions traveling to the end of RFQ). Thus the diffusion of these ions may be significantly less than that for the real neutral particles and its part which could come out of RFQ may be close to those for usual ions. No DC fields are applied in this case at the end of RFQ as they are not very effective in this case. However, it may be reasonable to apply some voltages between RFQ and the exit aperture like (16) and (17) shown in FIG. 1. Ions in this region would not have much possibilities to change their charge state which means that positive ions would be accelerated (by the fields as they are shown), the corresponding negative ions would be decelerated, and zwitter-ions would conserve their velocity. This property may be used further to distinguish the origin of recorded ions from initially positive, negative or from zwitterions. To prevent significant cluster formation a short path for the ions between the place of isolation and the exit orifice of RFQ region (18) is necessary so as not to allow the average ion velocity to come very close to the gas flow velocity (and thus for ions not to be excessively cooled). This average ion velocity for a given experimental conditions would be dependent on the averaged ratio of mass to collision cross section of ions and could be measured by multichannel recording in the TOFMS. To record zwitterions they should be converted to charged particles. It may be done, for example, by electron attachment to some positively charged site of a zwitterion if the pulse (77) shown in FIG. 7 is applied to electron impact ionizer anode (21). Also it is possible to do by producing of He+ions by electron impact inside the gas beam (19) in case the anode pulse has a view (22) shown in FIG. 1 and attachment of these ions to some negatively charged sites of the zwitterions. It may be reasonable also to decompose zwitterions by laser beam to produce pairs of positive and negative ions. In case it is done inside extraction region of TOFMS it could be possible to detect this pair in co-incidence since their parent ion is the zwitterion, therefore more reliable structural information may be measured in this case.

Figure 13:
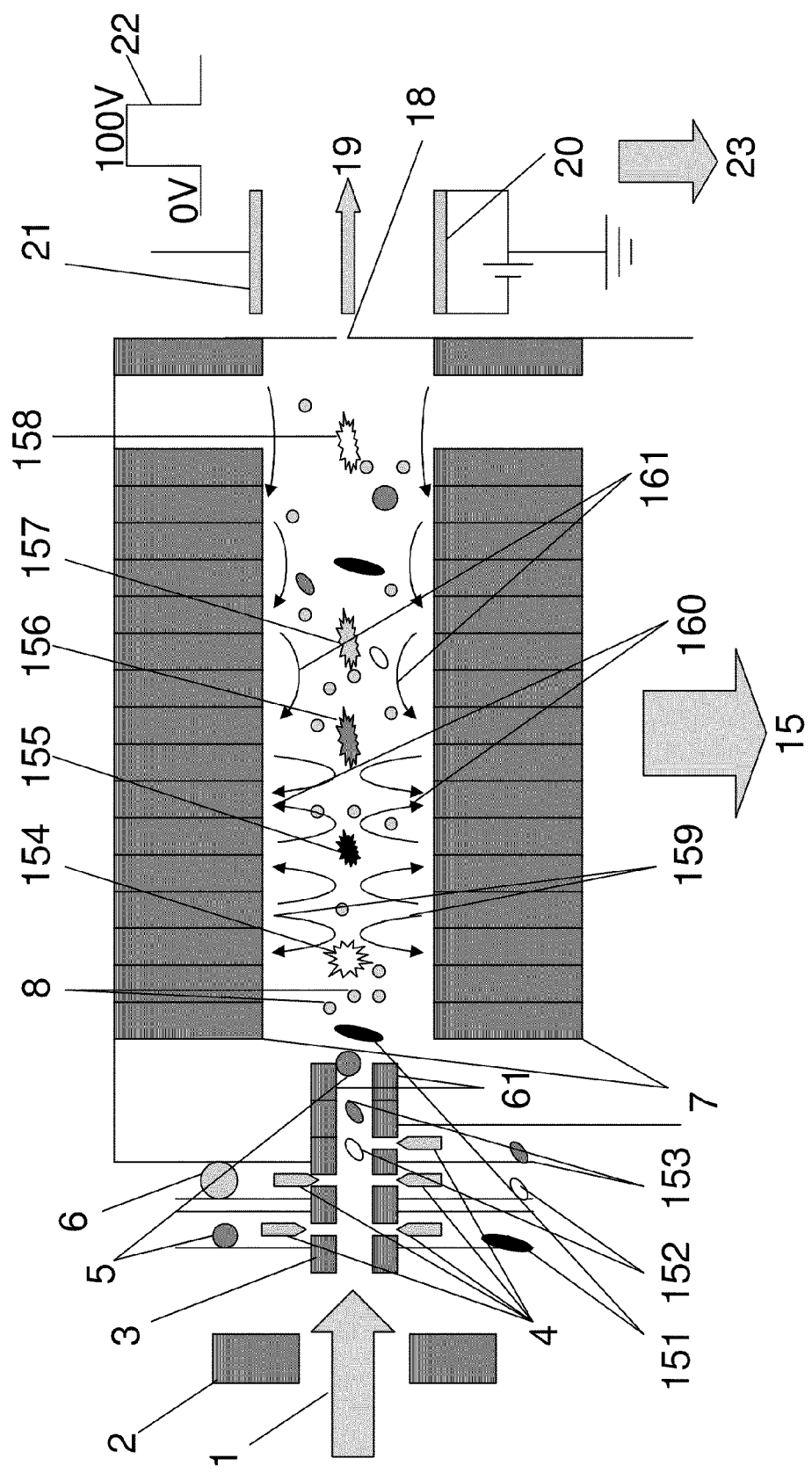
FIG. 13. Illustration of selection of desired biomolecules by providing conditions close to their isoelectric point.
Figure 14:
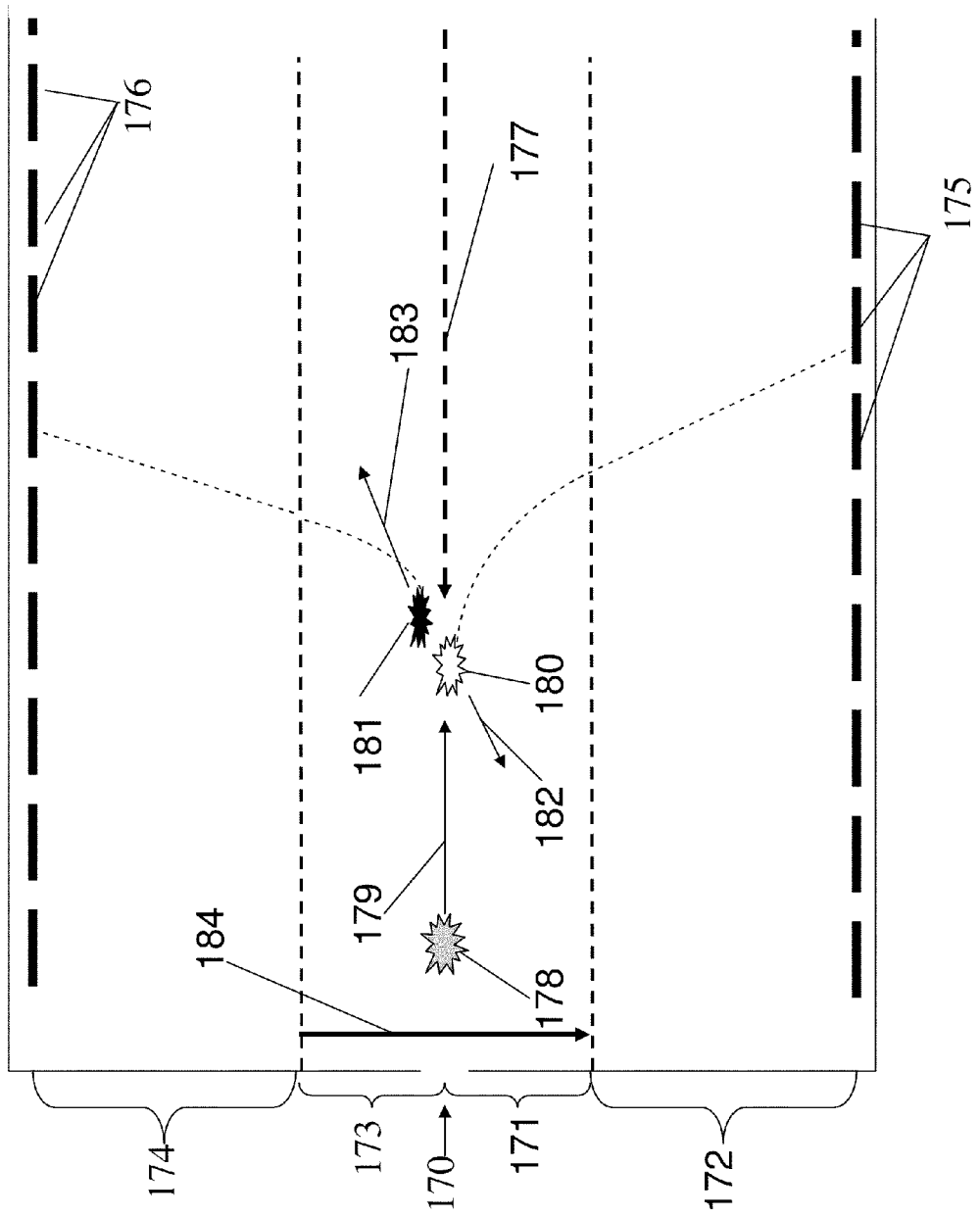
FIG. 14. Schematic view of a linear Bipolar Time-Of-Flight Mass Spectrometer (BiTOFMS) and coincident recording of zwitter-ions fragments produced by laser-induced dissociation.
Figure 15:
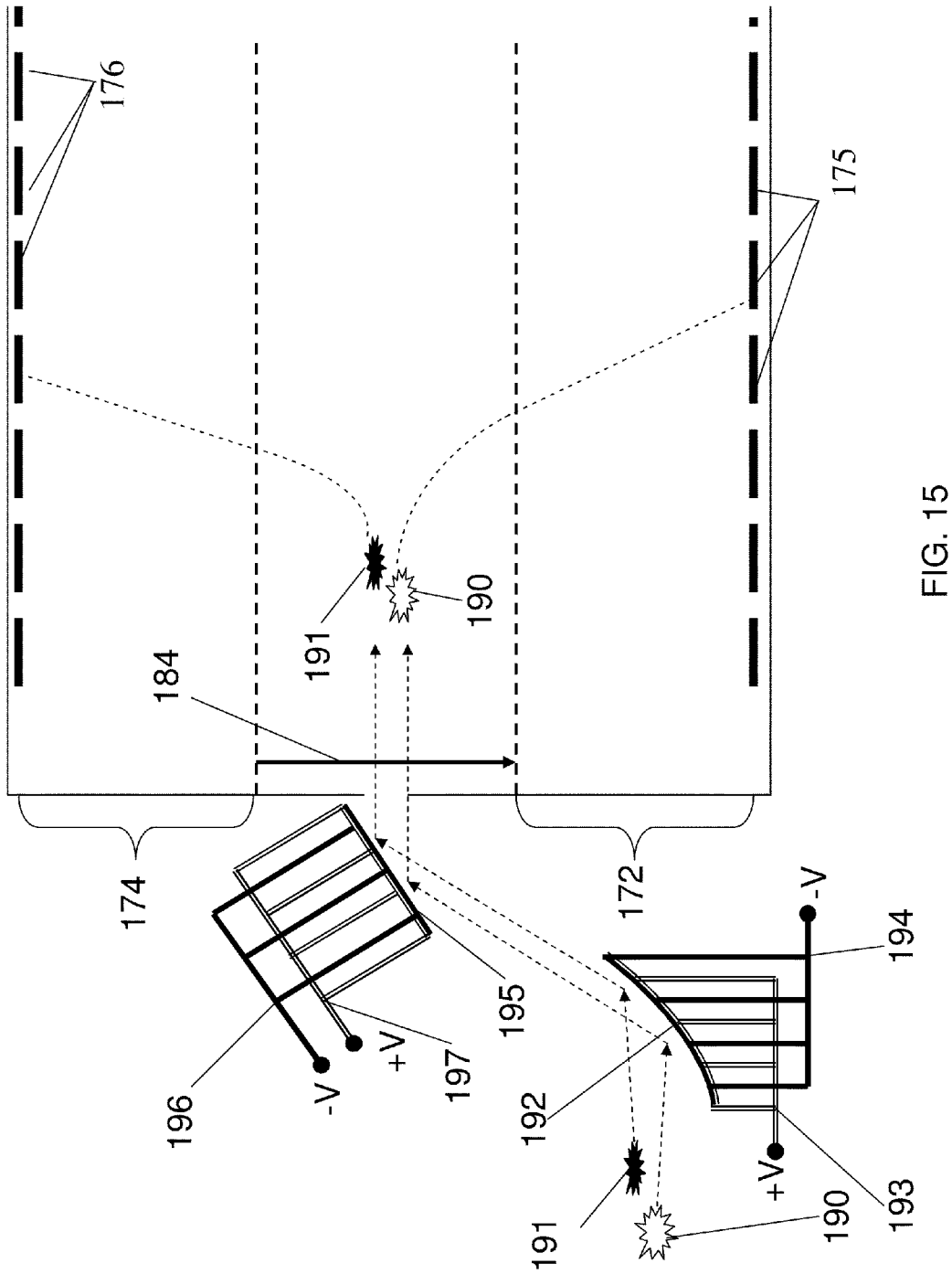
FIG. 15. Schematic view of ion mirrors for transformation of divergent bipolar ion flow into quasi-parallel beam followed by its insertion into a linear BiTOFMS.

To record such ion pairs as well as uncorrelated positive and negative ions, a Bipolar Time-Of-Flight Mass Spectrometer (BiTOFMS) shown schematically in FIG. 14. It is a simplified linear BiTOFMS. Reflectron type instruments of this kind are possible as well with both parts for positive and negative ions having tilted geometry. Ions (170) are directly inserted from exit orifice (18) FIG. 13 into the middle of acceleration region where electric field (184) is created for the time of ion extraction. Positive ions should be accelerated to the bottom multianode recording plane (175), negative ions—to the top one (176). The field "free" region for positive ions (172) is about twice as long as the acceleration region (171) for them, as well as this relation is valid for negative ions: the field length (173) is twice less than the field free gap (174). Between inserted ions some zwitterion (179) is shown at the beginning of its travel inside the BiTOFMS with some initial velocity (179). At some chosen time after the start of extraction of usual positive and negative ions (not to confuse them with the products of the zwitterions) under influence of laser beam (177) the zwitterion decomposes into positive (180) and negative (181) ions. In their center of mass reference system these ions have opposite velocities ((182) and (183)) whose magnitude is inversely proportional to the ion masses. These velocities are added to initial velocity (179) to give start velocities of ions for their acceleration in the field (184). According to their m/z values, start position, and start velocities they are recorded in due times by the corresponding channels of both recording systems of the BiTOFMS. As velocities like (179) should be close to the average velocity for all ions produced from the same parent molecules their estimation may be received by comparison of recording positions of ions of different m/z values as it was described earlier herein devoted to the measurement of ion cross sections. Comparing of recording positions of ions (180) and (181) for measured times of their motion to recording plates (175) and (176) would give some estimations for the axial components of velocities (182) and (183). As these velocities (and the axial components as well) should be inversely proportional to the ion masses (or their m/z values estimated from the times of recording) it gives a means for confirmation that these ions are produced from the same zwitterion. The sum of masses of these two ions would give the mass of the zwitterion (including some cluster shell). Comparison with "exact" mass of the molecule itself if it was measured before would give the mass and the composition of this shell and some estimation of orthogonal to recording planes components of ion velocities (182) and (183). Using these estimations for a number of such zwitterion decompositions it may be possible for known photon energy of the laser light to evaluate the effective strength of the corresponding bond which would include the average energy of electrostatic attraction of the separating ions (180) and (181) and probably the energy spent for removing of some cluster shell molecules. Having this information for different pairs of these ions some conclusions about zwitterion conformation could be done. Other mentioned ways of converting of zwitterions into recordable ions have no such clear possibilities. On the other hand in these cases it is possible to provide less divergence of the ion beam (170) and to have better resolution and accuracy of m/z measurements. As recordable ions are produced just after the RFQ exit it is possible to reflect them by a parabolic (or a proper cylindrical) mirror to convert a divergent ion beam into quasi-parallel one as it is described in co-pending U.S. patent application Ser. No. 11/441/766, filed May 26, 2006, for unipolar ions. However, in a case of bipolar ion flow, the mirror with a charged thin dielectric film described in U.S. patent application Ser. No. 11/441/766 will not be optimal. However, reflection of bipolar ions is possible from a surface polarized by alternating charges. This effect is similar to ion focusing by RF-field—ions moving quickly along a surface with changing potentials would be actually influenced by some fast alternating field. However, estimations show that randomly distributed positive and negative charges on some surface due to high enough average frequency of this field would not provide a strong enough repulsion force for ions having the energy (velocity) of motion orthogonal to the surface which is expected in our instrument. On the other hand, it is possible to fabricate effective ion mirror surfaces from thin layers of conductor and dielectric and to connect adjacent conductors to bipolar voltages of the same absolute values. Also it is possible to fabricate such structures from piezoelectric thin film structures with patterned electrodes. Ions in this case should move in directions close to the orthogonal to one to the layers. For velocities of ions of about 1000 m/sec (close to the velocity of helium gas flow in our case) the thickness between the layers of few tenths of mm would be suitable as it would be equivalent of the frequency of effective AC field of few MHz. Low voltages applied between these layers would be enough to reflect most ions and the voltages can be empirically optimized for ions of specific m/z. Thus it is also possible to increase the voltage on these layers in time so that the best field strength is present to reflect the mobility selected ions which are eluting from the cell at that time. If necessary, significantly stronger voltages may be applied without creating a glow discharge since the gas pressure in the region of their usage is low enough. FIG. 15 illustrates this idea. Positive (190) and negative (191) ions come to parabolic or cylindrical mirror (192). The focus of this mirror is located in the center of exit orifice (18) of RFQ shown in FIG. 13, for example. The mirror may be built from isolated conductor layers to which positive (193) and the same value negative (194) voltages are applied. Ions coming out of the orifice (18) are reflected from this mirror and form a quasi-parallel ion beam. This beam is reflected from the flat mirror (195) built in the same fashion as the parabolic mirror; from isolated conductor layers with positive (197) and negative (196) voltages applied to them. After this reflection positive (190) and negative (191) ions are then simultaneously inserted into the oTOFMS simultaneously measured by applying a pulsed field (184) which simultaneously accelerates them to the positive (175) and negative (176) multi-anode detector recording planes. Using more complicated system of mirrors, for example, one parabolic and two flat mirrors may allow one to recreate the same direction of the ion beam axis as that prior to the mirror system. Also, mirrors can be constructed with different shapes and combinations which we suggest as an alternative which can provide point to parallel focusing or point to point focusing using specially designed mirrors. An internal surface of ellipsoid of revolution is able to collect beams coming from one focus and project the beam into the a second focus. It is possible of course to coat some part of this surface by thin dielectric film which could be charged with one ion sign, but the more general way to construct such devices is with the interleaved electrodes in analogy to the mirrors shown in FIG. 15 by assembling of kapton foil electrode sections. An Alternative way to focus ions to the input orifice of an MS is to use this flexible circuit for producing of both mirrors in which their shapes can be obtained by constructing corresponding ellipsoids and cones having the desired focuses to provide focusing ions from the aperture (18) to the MS input orifice by point to point focusing. This is not useful for an oTOF instrument, but can be quite useful for any other mass spectrometer which does not depend on parallel ion beams. A cylindrical ellipsoid may be replaced by corresponding osculating circles without noticeable losses in focusing properties. In cases when additional differential pumping stages are necessary the point to point focusing mirror systems may be repeated any desired number of times. It is also possible to then replace the last set of elliptical mirrors with the corresponding parabolic mirrors of FIG. 15 which will then re-establish a quasi-parallel ion beam to transport ions without noticeable divergence for relatively long distance for insertion into an oTOFMS or into the trapping region of instruments such as an ICR or "Orbitrap".

In cases when isoelectric selection of biomolecules described in the previous section fail to provide pure isolation of the desired biomolecules, it is possible to combine it with previously described separation methods. Between a variety of possible versions of such combining it is possible, for example, to provide separation of biomolecules by two isoelectric points specific for the desired compound for two different experimental conditions. These conditions may include besides different temperatures some admixtures which may influence on charge exchange processes for biomolecules, for example, containing alkali metals which ions can substitute proton and compete with it for occupation of corresponding sites in the biomolecule. It is possible to provide the first isoelectric separation at the beginning of the ion guide as shown in FIG. 13 and to stop just separated ions by similar pair of retarding fields (159), (160) as shown in this figure but located at the end of the ion guide where these ions would acquire some nonzero average charge. By then changing the composition of the gas flow the condition for the second isoelectric separation are provided and ions with average zero charge are recorded as described in the previous section. Hopefully it would be enough to receive the flow of ions of the desired compound without noticeable admixtures. Otherwise more complicated schemes of multistage separation could be performed. Some of the methods described by Vandekerckhove, et al. in 2005 (U.S. Pat. No. 6,908,740) for liquid phase specific chemical and/or enzymatic alteration of selected types of peptides which are suitable for gas phase implementation may be used with the present invention. In case these alterations provide significant change in mass of some peptides additional separation may be achieved by resonant rotating field excitation of ions. If charging properties of some molecules are changed isoelectric separation may give different results comparing to those without any alterations.

The bipolar TOFMS and new approaches for isolation of desired biomolecules described in previous sections and the concept of simultaneous measurement of positive and negative ions from the same sample (disclosed in co-pending U.S. patent application Ser. Nos. 11/441,766 and 11/441,768) may be implemented in another way as described below. Instead of moving of positive and negative ions from the trapping region in opposite direction to different TOFMS instruments dedicated for separate recording of positive and negative ions, the positive and negative ions together are directed to the single bipolar TOFMS To accomplish this, RF-voltages are decreasing along the entrance mobility tubes and are applied to the sections of these tubes. Ions of both sign would be pushed in direction of decreasing voltages and for strong enough gradients, this would overcome the counter gas flow coming from these entrance tubes. For a narrow range of m/z values and mobilities a constant set of these RF-voltages may be applied allowing transport of the ions inot the BiTOFMS. In this case this system may work in "continuous" mode. This separation may be not so important in case of analysis of mixtures of multicharged bioions as they may be for isolating by rotating field on the base of their m/z values and further separation on the basis of their isoelectric points as described before. However, analysis of complex bioion mixtures with broad distribution of ions in their m/z values and mobilities could not be done effectively for a single set of RF-voltages. In this case smaller values and gradients of these voltages may be used for relatively small ions whereas larger values and larger gradients (or reduced frequencies of RF-voltages) may be used for larger ions. Also for some cases additional separation of the ions by their travel time from the trapping region to TOFMS may be useful for some kind of measurements. In this case in order to provide a "pulse" mode measurements, an RF-voltage plug applied before the trapping region may be switched on for the time of ion insertion into the entrance tubes and so prevent the next portions of ions from coming into the trapping region which would spoil the previous ion separation. As ion decomposition as well as other ion transformations may be performed under controllable conditions inside the RF-quadrupole CID (Collision Induced Dissociation) tubes may be omitted and the motion of ions of both signs inside the exit tubes may be provided by some gradient of RF-voltages applied to the sections of these tubes. Focusing of ions and their rotation excitation are provided independently of the ion sign with rotating of ions of different signs simply having a phase shift being equal to $\pi$ or 180°. Stopping of ions of both signs inside RFQ may be provided by corresponding RF-voltage plugs applied between adjacent sections of RFQ rods.

Previously described isolation of ions by using a resonant rotation field may be performed with less efficiency and resolution in case of absence of supersonic gas flow inside RFQ. In this case DC, RF or AC voltage plugs should be adjusted to stop ions rotating close to rods and allow travel along the RFQ axis for non-resonant ions under influence of small longitudinal electric field. Addition, in necessary cases, of heavy admixtures and an increase of the rotation field would result in heating of ions and in their decomposition. Ion-fragments can come out of resonance of rotating field and come to the RFQ axis. By use of an appropriate voltage plug it is possible to stop these ions near the axis and after finishing of decomposing of primary ions by corresponding rotating excitation. It is thus possible to select the desired product ions for further decomposition. The remaining ions may be transported to TOFMS. This procedure may be repeated the desired number of times. Thus, MS$^n$ technique may be implemented in the present invention also.

Figure 16:
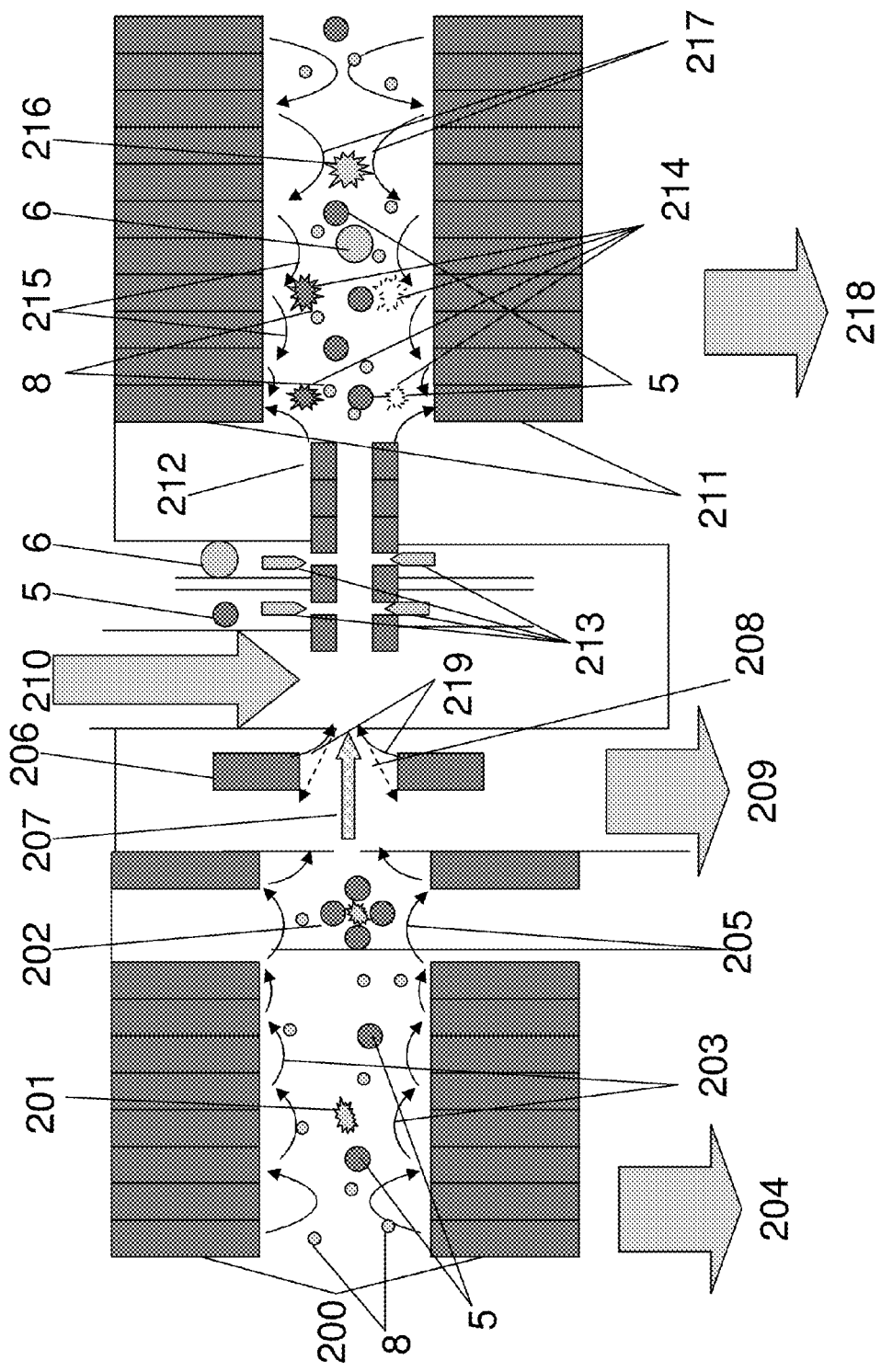
FIG. 16. Schematic view of coupling of two adjacent supersonic gas flow RFQ ion guides in series showing independent trapping in the second RFQ of the ion products received from the first RFQ.

An important advantage of the method and apparatus disclosed above is the isolation of ions and their transformation since it is a possible to initially trap a chosen set of ion types and then investigation them each in turn. By contrast, conventional methods usually can only investigate ions of one type (which are subjected for a given time to collision induced dissociation, for example) during which time all other initial ions are lost. To overcome this limitation Loboda, et.al. in 2005, US Patent Application 20050253064 A1, suggested a method of mass selective axial ejection of ions from linear ion trap by changing of ion dragging forces provided by DC and AC fields. However, this approach includes as a first step trapping of all ions produced in previous stage of the system. It is desirable also to provide a possibility of further investigations of product ions received at least from some types of the primary trapped ions. Unfortunately, trapping of the product ions in this case (as it is described above) may be complicated when m/z of these ions are close to those for some primary trapped ions as such ions may be confused in further steps of investigation. To solve this problem it is possible to use instead of a single RFQ ion guide with supersonic gas flow some sequence of such ion guides when the first ion guide accepts ion flow from a mobility cell or directly from some ion source and the last one delivers ions into a TOFMS. Schematic of connection between a pair of these adjacent guides is shown in FIG. 16. The product ions (201) and (202) produced in the left ion guide (200) are moving under influence of the supersonic flow inside this guide of helium atoms (8) with possible admixtures such as argon (5) and possible electric field along RFQ axis (203). Under optional focusing field (205) these ions (207) come out of this guide and overcome the counter helium flow (208) from the right ion guide under possible help of electric field (219) between focusing electrodes (206) and entrance plate of the right ion guide. The main part of initial helium flow (210) inserted into the right ion guide is directed into sectioned tube (212) where as for previous ion guides some admixtures like argon (5) and xenon (6) can be inserted into the flow. The gas coming from the tube (212) turns into a supersonic gas flow. Under the influence of corresponding rotating fields the desired product ions (214) are trapped at the beginning of the RFQ (211). They are stopped inside RFQ by electric field (215) as described before. After trapping of desired product ions is finished the trapped ions may in turn be moved to a place of further transformation (216) provided by a corresponding electric field (217). Their products may then be trapped and investigated in additional ion guides as just described. Such operations may be repeated a desired number of times restricted only by the number of the ion guides connected in series before the TOFMS. To provide the necessary conditions for the desired gas flows the corresponding pumps such as (204), (209) and (218) should be used in the system.

Additional capabilities for getting structural information about large enough bio-ions may be provided by somewhat the more sophisticated operation of an electron impact ion source located after the exit orifice of the RFQ ion guide than that described before. A simplified schematic of this ion source with indirect heated cathode (75) is shown in FIG. 7. Using as cathode material of lanthanum hexaboride crystal allows one to have a large enough density of electron current (few mA per square cm) and relatively low width of electron energy distribution (close to 0.1 eV). Simple estimations show that for cathode length of about 1 cm, a large bio-ion with collision cross section of about 1000 Å$^2$, moving with helium flow across a continuous electron beam with current density 2 mA/cm$^2$ would be impacted by an electron with probability close to 0.1. The probability is large for observing products produced by two or more electron impacts. The expected result of such impact with electron with energy of few eV (less than ionization potential of the biomolecule— typically close to 10 eV) would be dissociation of some bond in the molecule probably close to location of the electron impact. To provide this dissociation the energy of electron impact should not be less than the corresponding bond strength. By recording of yields of ions produced by dissociation of some bonds in the bio-ion for different electron energies after processing of thus received ion appearance curves it would be possible to get seeming thresholds for the corresponding bond dissociations. The procedure of processing may be close to that described in our old paper devoted to processing of ionization efficiency curves for some simple molecules and radicals (Raznikov, et. al. Int. J. Mass Spectrom. Ion Proc. v. 71, 1986, p. 1-27). Precision for ionization threshold determinations noticeably better than 0.1 eV was demonstrated in this work. It is necessary to take into account that dissociation thresholds determined in such a way for given bio-ion may deviate significantly from the corresponding bond strengths. The main reason for that may be a changed kinetic energy of impacting electron in the local electric field of the ion. For example on the distance of about 10 Å from location of positive charge in the ion electron impact energy would be more than its initial energy for about 1 eV (if polarization influence of atomic arrangement of the ion may be neglected). In case the corresponding energies of bond dissociations were determined before by ion heating under influence of heavy admixtures to the helium flow as described already here then comparison with electron impact thresholds would give some information about the distribution of local electric field inside the considered bio-ion. It may give a possibility to draw important conclusions about the space structure of bio-ions in gas phase which is not possible to do by other methods. Besides that when dissociation of some bond in the bio-ion produces not one but a pair of recordable ions the coincidence of the corresponding appearance curves would give additional confirmation of the origin of the product ions from the same parent ion with expected sum of these ion masses being equal to the mass of the parent ion. Alternatively to recording of product ions for different electron energies it is possible for given electron energy to change the temperature of the ions by inserting of different retarding (or accelerating) fields at the end of RFQ and/or changing contribution of heavy atoms in the helium flow. Plotting of relative ion yields in logarithmic scale for inverse ion temperature hopefully would show Arrhenius type curves as for the described similar situation when photoionization of biomolecules was investigated (Wilson, et. al., J. Phys. Chem. A v. 110, 2006, pp. 2106-2113). Angle coefficients derived from these curves would give the activation energies for the dissociation of corresponding bonds what usually is considered as a good estimation of the bond strengths for pure thermal decomposition. For the case of electron impact it may be expected that these activation energies would be close to differences between the corresponding bond strengths and the energy of electron in place of impact. Comparison of results of these kinetic measurements with estimations received via processing of ion appearance curves under varied electron impact energy may give better understanding of ion decomposition processes occurring in the considered conditions.

The applications of this instrumentation and methods are not restricted to analysis of the structure and mass of gas phase ions. This invention may also be used for isolation, cooling and selected area soft landing depositions of mass and mobility selected ions. Also, as in analogy to combining this instrument with a highly monochromatic electron impact ionizer, the instrument can also be combined with other instruments and techniques for ionization or known to those skilled in the art. Among some of these examples would be the use of the long trapping times and high mass capability, which would allow co-measurement of luminescence lifetimes and quantum yields while the mobility and mass-selected ions are rotating in the trap. In particular this can be powerful when either the intrinsic luminescence or the luminescence from a luminescence tag, including but not limited to aromatic molecules and lanthanide (especially Eu), which among other uses, are useful in determining water salvation chemistries of isolated ions. Since ions with a salvation shell can be prepared and isolated and trapped, the co-application of techniques such as circular dichroism, real-time x-ray scattering, and photoelectron spectrometry using either standard excitation sources or synchrotron light sources could provide extremely useful measurements of the structure of the trapped solvated and unsolvated gas phase ions in a way which would indicate their probable in-vivo conformations. Photo-ioniztion and photo-fragmentation of ions within the rotational trapping regions or trapping regions within the dense gas flow are also possibilities.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An apparatus for the analysis of gaseous ions and neutral species and mixtures thereof, said apparatus comprising:
    an ion source for the production of gaseous ions and neutral species and mixtures thereof;
    a gas flow formation region fluidly coupled to said ion source, said gas flow formation region comprising a sectioned capillary having at least two electrodes, said gas flow formation region operable to accept ions and/or neutral species from said ion source;
    at least one sectioned radio-frequency multipole ion guide fluidly coupled to said gas flow formation region, said sectioned ion guide comprising a plurality of electrically isolated electrode sections;
    an exit orifice fluidly coupled to said at least one sectioned radio-frequency multipole ion guide, wherein said multipole ion guide produces a controlled DC electric field and/or an AC rotating field which traps specific ions from said gas flow and said mulitpole ion guide produces a resonant rotating field which extracts specific ions from said gas flow and causes said specific ions to follow a rotational orbit around the central axis of said multipole ion guide and whereby switching off the DC electric field, the AC rotating field and/or the resonant rotating field releases desired ions back into said gas flow; and,
    a detector fluidly coupled to said exit orifice; and,
    an electron source fluidly coupled to said exit orifice and to said detector, wherein said electron source is a pulsed electron source, a continuous electron source, or a combination thereof.

2. The apparatus of claim 1, wherein the electron source is an electron impact ion source.

3. The apparatus of claim 2, wherein the electron impact ion source is a monochromatic electron impact ionizer.

4. The apparatus of claim 1, wherein the ion source is fluidly coupled to an indirect heated cathode.

5. The apparatus of claim 4, wherein the indirect heated cathode comprises lanthanum hexaboride crystal.

6. The apparatus of claim 4, wherein the indirect heated cathode has a length of about 1 cm.

7. The apparatus of claim 1, wherein said detector is a mass spectrometer.

8. The apparatus of claim 7, wherein said mass spectrometer is an orthogonal time-of-flight mass spectrometer.

9. The apparatus of claim 8, wherein said orthogonal time-of-flight mass spectrometer comprises a position sensitive multi-anode detector.

10. the apparatus of claim 8, wherein said orthogonal time-of-flight mass spectrometer is a bipolar time-of-flight mass spectrometer.

11. A method of analyzing gaseous ions, neutral species or mixtures of ions and neutral species comprising:
   introducing said ions and/or neutral species into a gas flow formation region to form a gas flow of said ions and/or neutral species, said gas flow formation region comprising a sectioned capillary having at least two electrodes;
   introducing said gas flow of ions and/or neutral species into at least one sectioned radio-frequency multipole ion guide, said sectioned ion guide comprising a plurality of electrically isolated electrode sections;
   applying voltage selected from the group consisting of DC voltages, AC voltage, RF voltages, and any combination thereof, to one or more sections of said at least one sectioned radio-frequency multipole ion guide, wherein said step of applying voltage to said multiple ion guide comprises producing a controlled DC electric field and/or an AC rotating field which traps specific ions from said gas flow and producing a resonant rotating field which extracts specific ions from said gas flow and causes said specific ions from said gas flow and causes said specific ions to follow a rotational orbit around the central axis of said multipole ion guide and switching off the DC electric field, the AC rotating field and/or the resonant rotating field to release desired ions back into said gas flow;
   impacting said gas flow of ions with a second flow of electrons wherein the impacting step disassociates the ions present in the said flow of ions producing a disassociated species; and,
   detecting said gas flow of ions, disassociated species and/or neutral species,
   wherein the second flow of electrons is continuous, pulsed or any combination thereof.

12. The method of claim 11, wherein the second flow of electrons is produced with a monochromatic electron impact ionizer.

13. The method of claim 12, wherein said step of applying voltage to said ion guide further comprises producing a gradient DC field which traps said ions following a rotational orbit in a region of the ion guide.

14. The method of claim 13, wherein said step of applying voltage extracts and traps ions of one or more m/z values and ion mobility cross sections.

15. The method of claim 14, further comprising the step of photo-ionizing the said ions.

16. The method of claim 14, further comprising the step of photo-fragmenting the said ions.

17. The method of claim 14, further comprising the step of measuring the luminescence lifetimes of the said ions.

18. The method of claim 14, further comprising the step of measuring the luminescence quantum yields of the said ions.

19. The method of claim 12, wherein said step of introducing said ions and/or neutral species into a gas flow formation region comprises introducing said ions and/or neutral species into a supersonic gas flow.

20. The method of claim 12, further comprising applying a DC voltage between the last electrode of said sectioned capillary and first electrode section of said radio-frequency multipole ion guide.

21. The method of claim 12, further comprising the steps of applying a decreasing electric field in the direction of the gas flow in said radio-frequency multipole ion guide and measuring the mobility cross-section of said ions.

* * * * *